(12) United States Patent
Sadlo et al.

(10) Patent No.: US 10,485,694 B2
(45) Date of Patent: Nov. 26, 2019

(54) PROTECTIVE SHEATH

(71) Applicant: GummiWerks LLC, Las Vegas, NV (US)

(72) Inventors: Frank C. Sadlo, Las Vegas, NV (US); Keh How Lai, Bangkok (TH); Gabriel A. Bear, Austin, AR (US)

(73) Assignee: GummiWerks LLC, Las Vegas, NV (US)

( * ) Notice: Subject to any disclaimer, the term of this patent is extended or adjusted under 35 U.S.C. 154(b) by 165 days.

(21) Appl. No.: 14/565,336

(22) Filed: Dec. 9, 2014

(65) Prior Publication Data

US 2015/0157494 A1 Jun. 11, 2015

Related U.S. Application Data

(60) Provisional application No. 61/913,939, filed on Dec. 10, 2013.

(51) Int. Cl.
*A61F 6/00* (2006.01)
*A61F 6/06* (2006.01)

(52) U.S. Cl.
CPC .................................. *A61F 6/065* (2013.01)

(58) Field of Classification Search
CPC .... A61F 6/02; A61F 6/04; A61F 6/065; A61F 2006/043; A61F 2006/045; A61F 2006/048; A61F 6/00; A61F 6/06; A61F 6/08; A61F 6/20; A61F 2006/041; A61F 2006/042; A61F 2006/047; A61F 2006/049; Y10S 128/918; A61H 19/34; A61H 19/32; A61H 19/40; A61H 19/44; A61H 19/50; B29L 2031/7538

USPC ....... 128/844, 918, 842, 917, 830, 834, 837, 128/859, 898; 600/38, 39, 41; 604/330, 604/347; 427/2.3
See application file for complete search history.

(56) References Cited

U.S. PATENT DOCUMENTS 4,945,923 A  *  8/1990  Evans ..................... A61F 6/065
                                                  128/837
4,964,416 A  *  10/1990 Foldesy .................... A61F 6/04
                                                  128/842

(Continued)

FOREIGN PATENT DOCUMENTS

GB     2226957       *  7/1990  ............... A61F 6/04
WO     97/30668         8/1997
WO     2006/102503     9/2006

OTHER PUBLICATIONS

Corresponding European Patent Application No. 14870253.3; Office Action dated Jul. 18, 2017, 7 pages total.

(Continued)

*Primary Examiner* — Adam Baker
(74) *Attorney, Agent, or Firm* — Craig R. Miles; CR Miles P.C.

(57) ABSTRACT

A protective sheath for use within a vaginal canal of a female user, the protective sheath including a flexible tubular body having a body medial portion disposed between a body closed end portion and a body open end portion; and an annular flange extending radially outward from the body open end portion, the annular flange terminating in an annular flange edge having an elliptical annular flange edge perimeter, whereby the elliptical annular flange edge perimeter configures to overlay a portion of a vulva of the female user.

20 Claims, 23 Drawing Sheets

(56) References Cited

U.S. PATENT DOCUMENTS

| | | | |
|---|---|---|---|
| 5,036,863 A | 8/1991 | Wheeler | |
| 5,074,314 A * | 12/1991 | Wilson | A61F 6/04 128/844 |
| 5,094,250 A | 3/1992 | Hessel | |
| 5,163,447 A * | 11/1992 | Lyons | A61F 6/04 128/844 |
| 5,318,043 A * | 6/1994 | Burr | A61F 6/04 128/844 |
| 5,454,379 A * | 10/1995 | Shepherd | A61F 6/02 128/842 |
| 5,490,519 A | 2/1996 | Hessel | |
| 5,623,946 A | 4/1997 | Hessel | |
| 5,992,415 A * | 11/1999 | Alla | A61F 6/065 128/830 |
| 6,182,661 B1 * | 2/2001 | Solanki | A61F 6/04 128/844 |
| 6,223,747 B1 * | 5/2001 | Rudge | A61F 6/065 128/844 |
| 6,341,607 B1 * | 1/2002 | Couvreur | A61F 6/065 128/830 |
| 6,569,083 B1 * | 5/2003 | Kassman | A61B 5/41 128/842 |
| D603,039 S | 10/2009 | Resnic | |
| 7,726,316 B1 * | 6/2010 | Pope | A61F 6/065 128/830 |
| 7,814,913 B2 * | 10/2010 | Osterberg | A61F 6/065 128/830 |
| 8,100,128 B2 | 1/2012 | Pope | |
| 8,136,528 B2 | 3/2012 | Resnic | |
| 8,431,055 B2 | 4/2013 | Platt et al. | |
| 8,667,968 B2 | 3/2014 | Resnic | |
| 2002/0038658 A1 * | 4/2002 | Austin | A61F 6/065 128/830 |
| 2003/0124354 A1 | 7/2003 | Vistins | |
| 2004/0107969 A1 * | 6/2004 | Tam | A61F 6/065 128/830 |
| 2007/0175484 A1 * | 8/2007 | Staab | A61F 6/04 128/844 |
| 2009/0007921 A1 * | 1/2009 | Kanno | A61F 6/00 128/844 |
| 2010/0252052 A1 | 10/2010 | Kettles et al. | |
| 2011/0303226 A1 * | 12/2011 | Resnic | A61F 6/065 128/844 |
| 2012/0152258 A1 | 6/2012 | Resnic | |
| 2013/0174852 A1 * | 7/2013 | Resnic | A61F 6/04 128/844 |

OTHER PUBLICATIONS

U.S. Appl. No. 61/913,939, filed Dec. 10, 2013.
AVN. Pleasurable Female Condoms on the Drawing Board; Article by AVN Staff. Website, http://business.avn.com, originally downloaded Nov. 7, 2014, 3 total pages.
Bloomberg. Female Condoms' New Fit Adds Pleasure to Fight Disease; Article by N. Khan et al. Website, http://www.bloomberg.com, originally downloaded Nov. 7, 2014, 3 total pages.
Impatient Optimists. Air-Infused Female Condoms; Article by M. Seibel. Website, http://wwww.impatientoptimists.org, originally downloaded Nov. 7, 2014, 3 total pages.
Salon.com. Bill Gates' pleasurable female condom is almost here; Article by J. Kutner. Website, http://www.salon.com, originally downloaded Nov. 7, 2014, 2 total pages.
PCT International Application No. PCT/US2014/069493, filed Dec. 10, 2014.
PCT International Application No. PCT/US2014/069493; ISR and WO dated May 15, 2015, 19 total pages.
FC2. About FC2. Website, https://fc2.us.com, originally downloaded May 26, 2017, 5 pages total.
Female Condom Market Intelligence. WHO/UNFPA Prequalified Female Condoms. Website, http://fcmi.org, originally downloaded May 19, 2017, 4 pages total.
Female Condom Market Intelligence. Other Female Condoms. Website, http://fcmi.org, originally downloaded May 19, 2017, 3 pages total.
Female Condom Market Intelligence. Female Condoms on Development. Website, http://fcmi.org, originally downloaded May 19, 2017, 2 pages total.

* cited by examiner

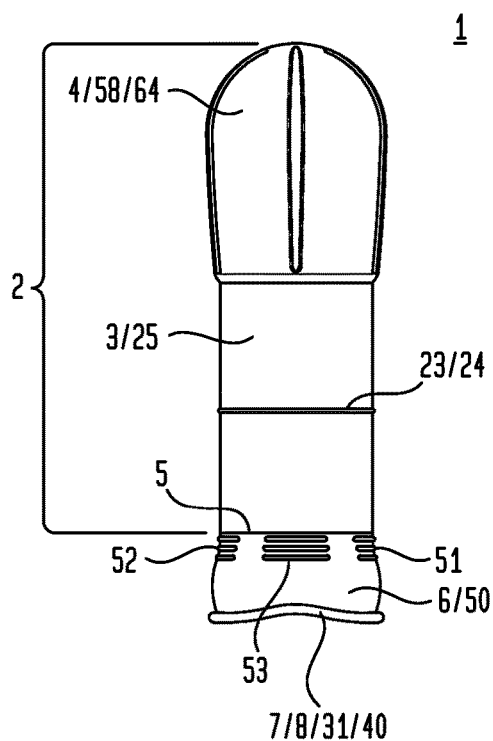
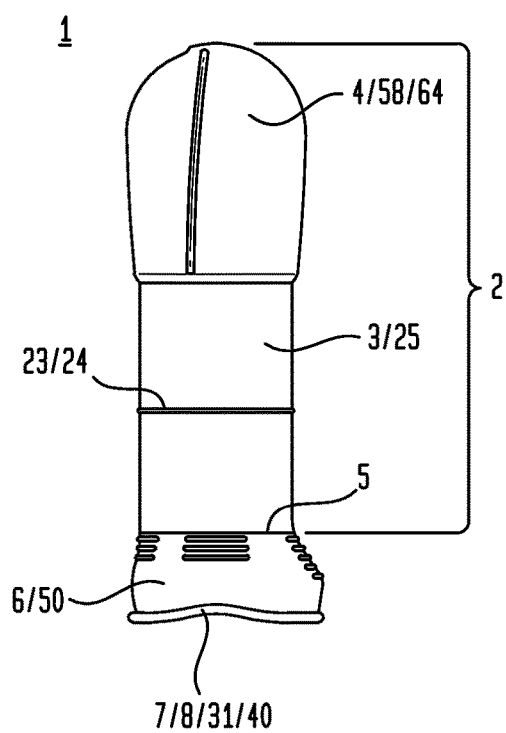

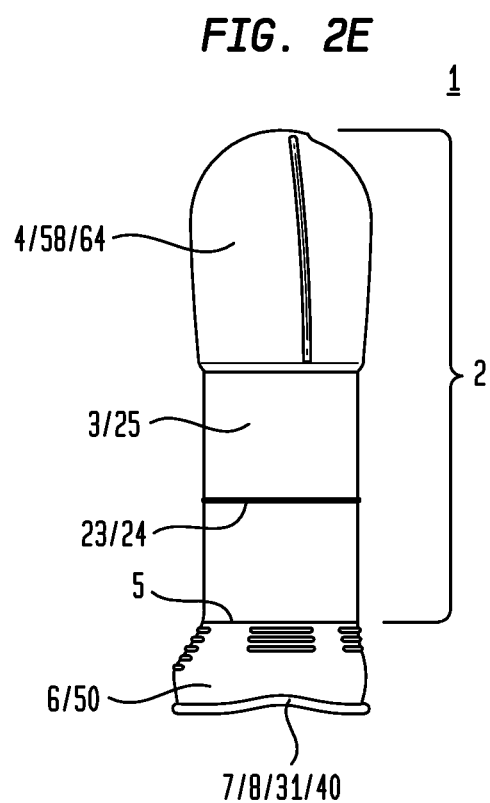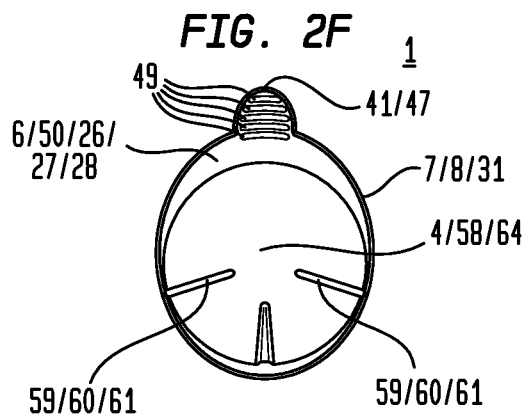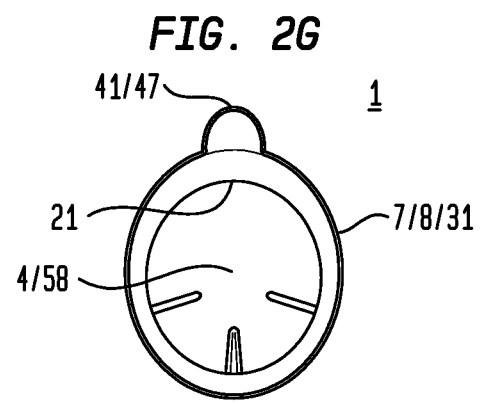

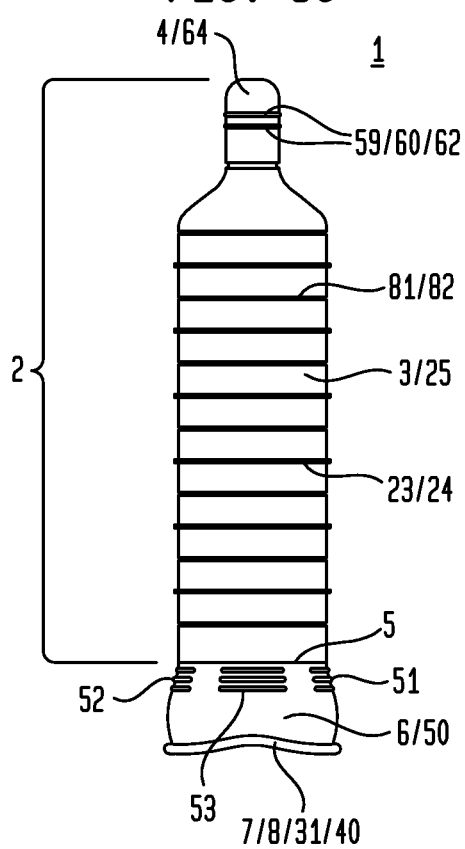
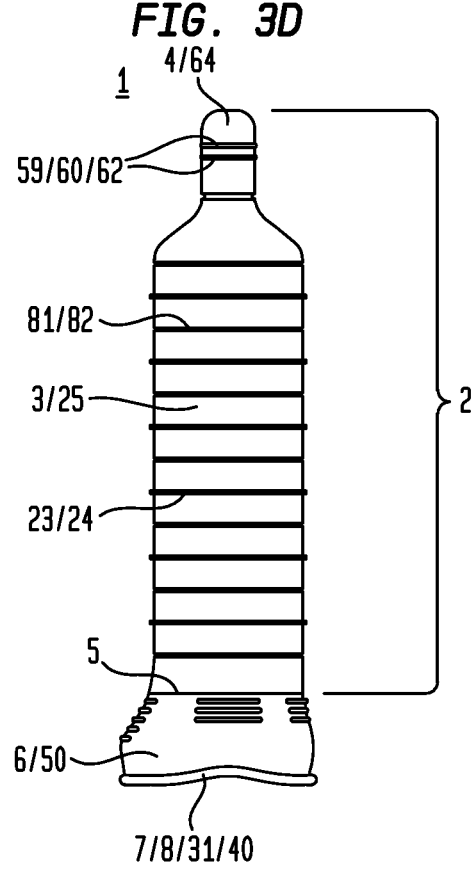

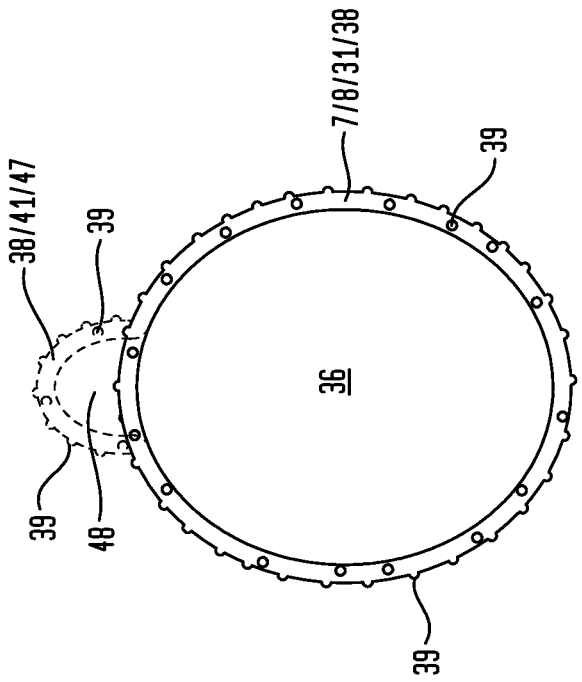
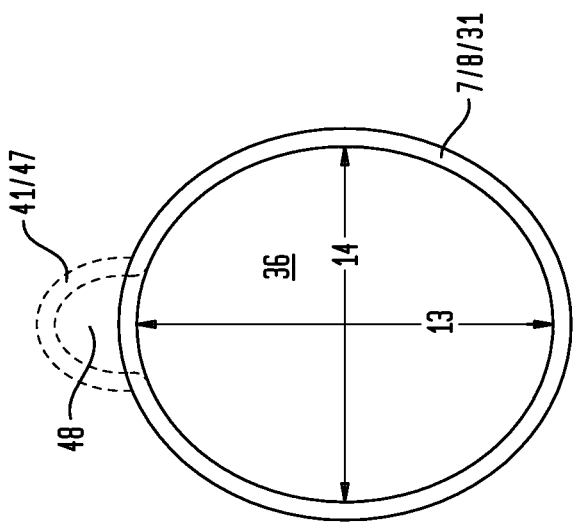

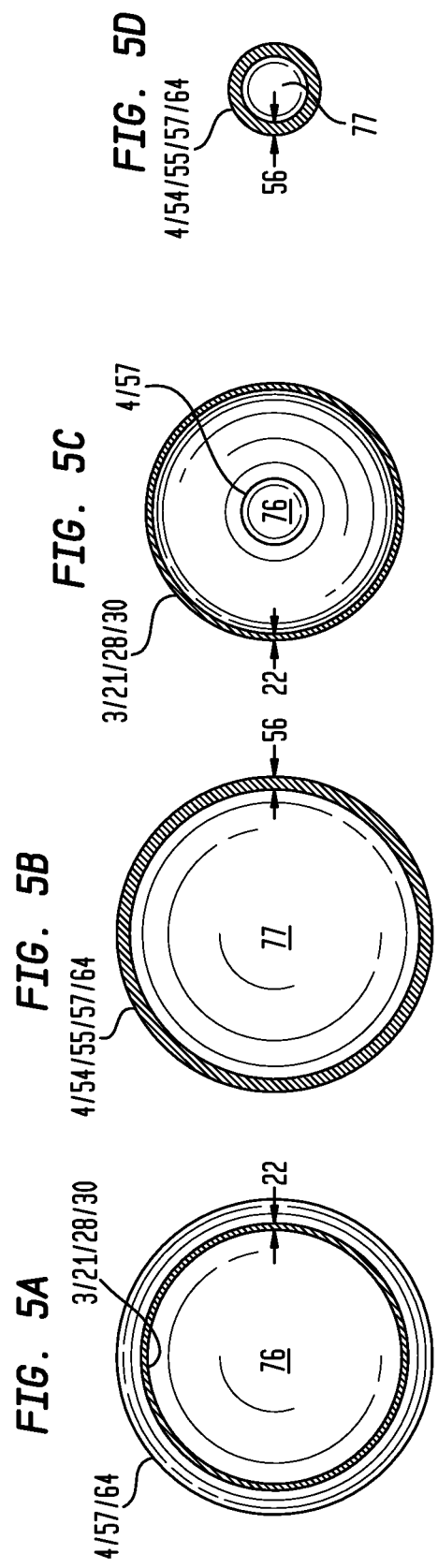

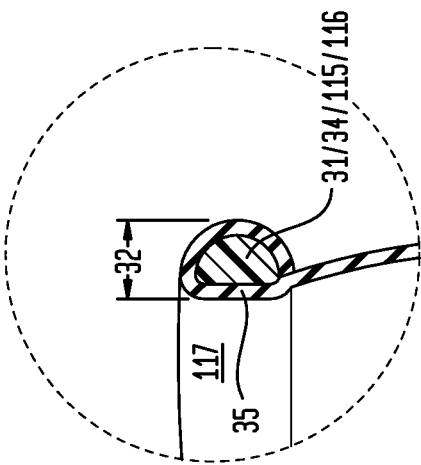
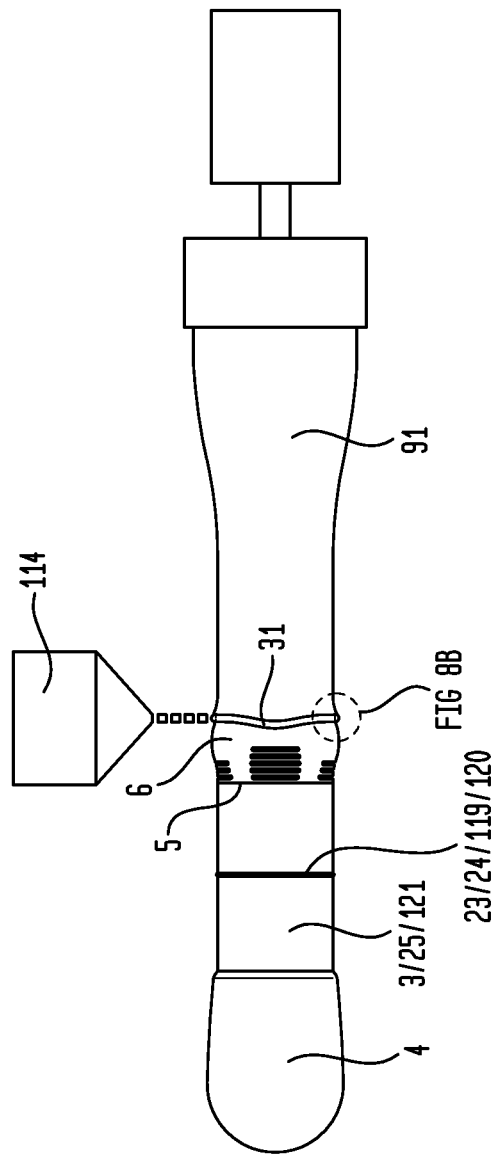

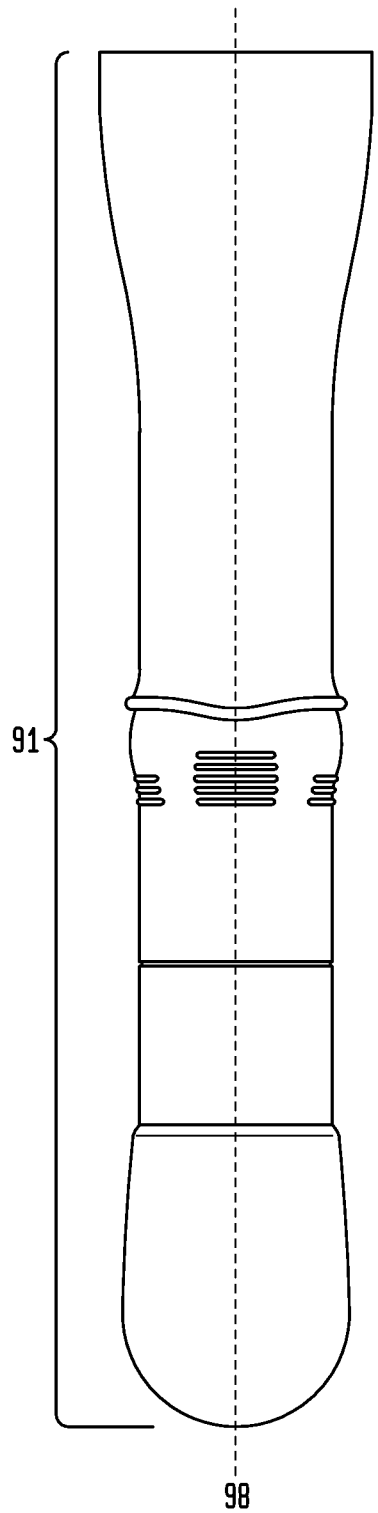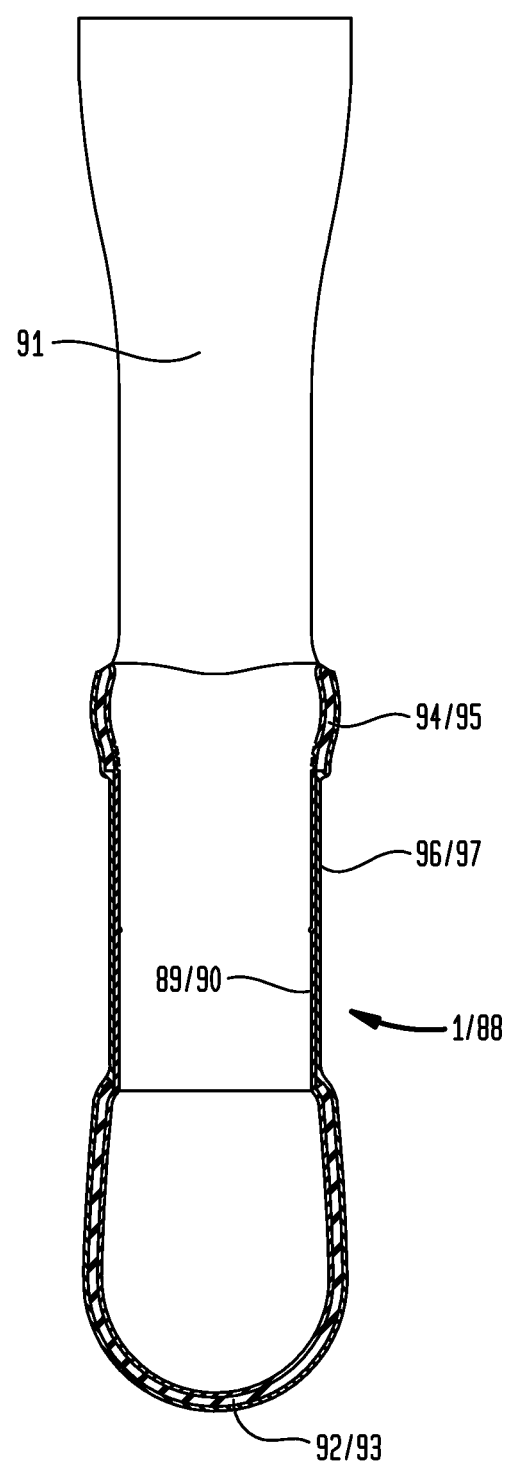

FIG. 14A
FIG. 14B
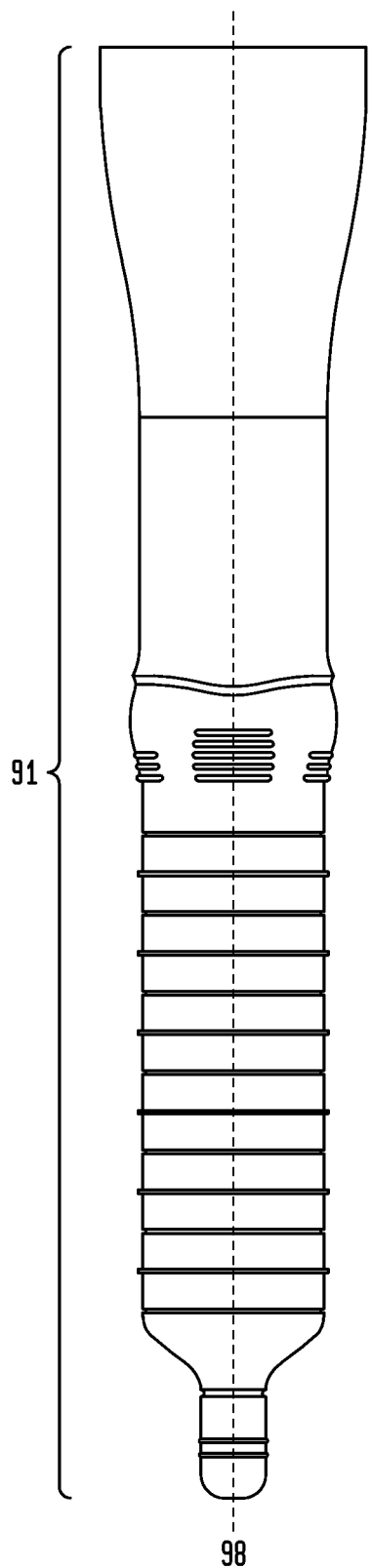
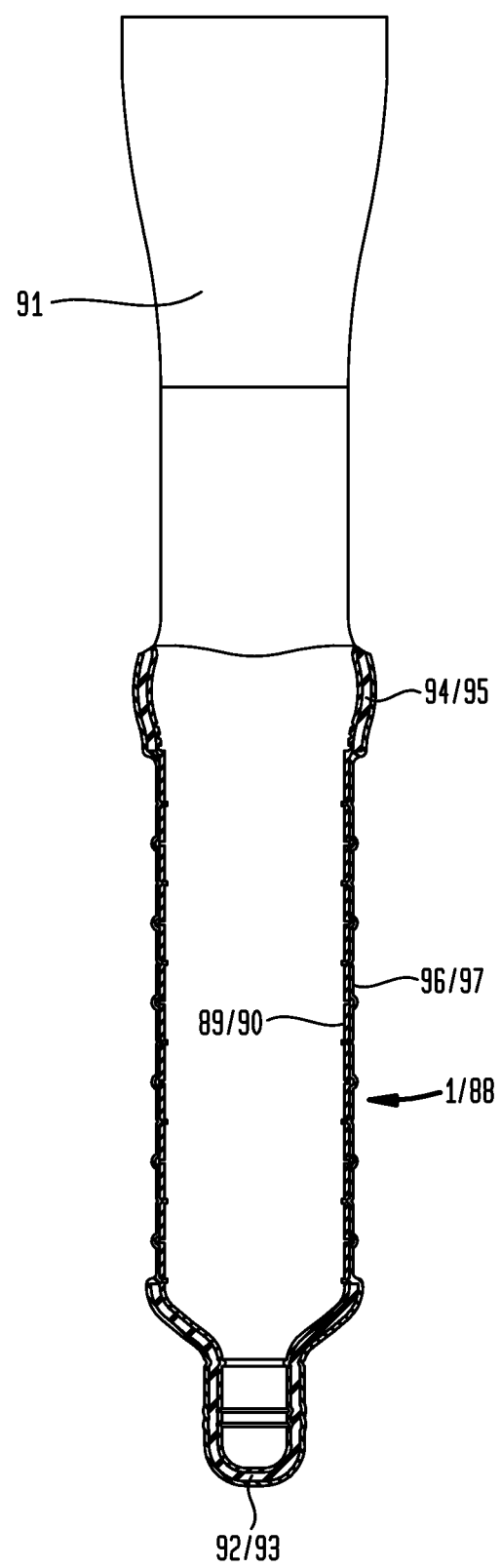

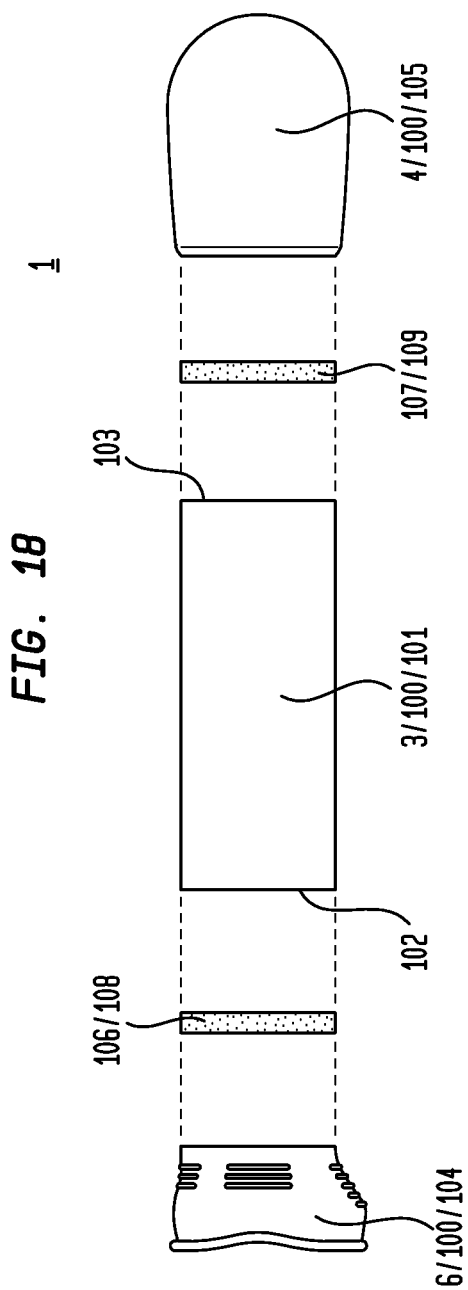

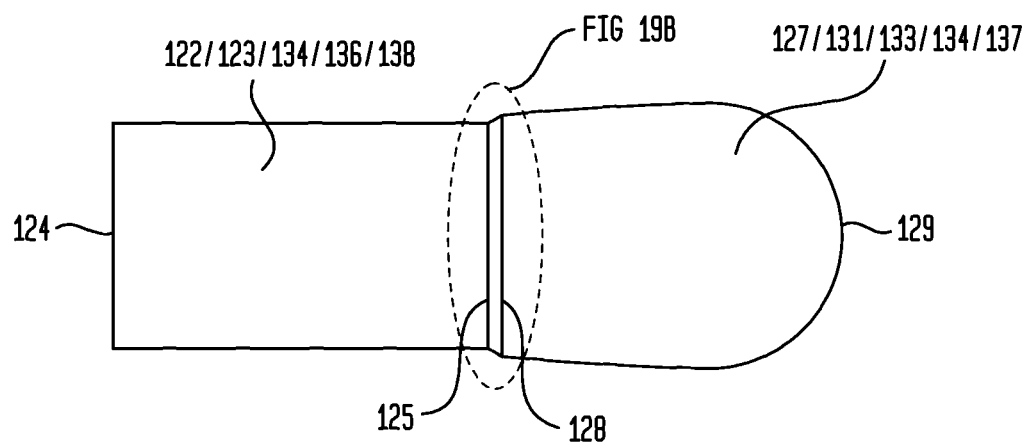
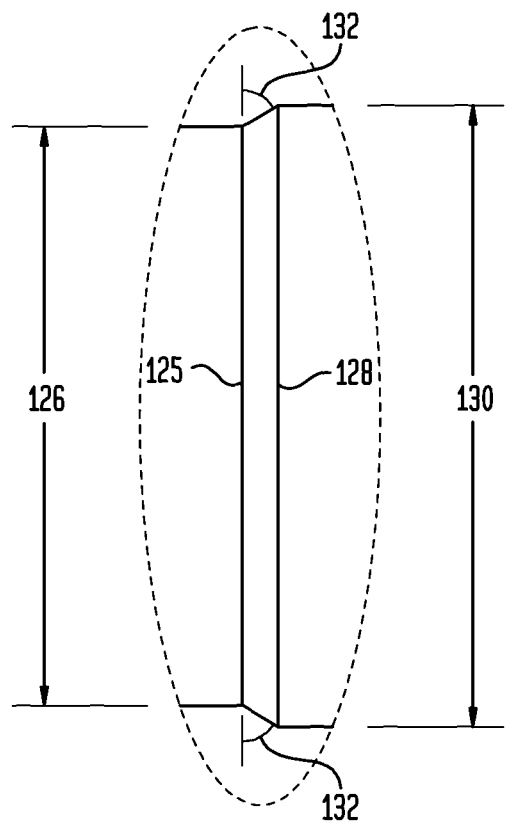

PROTECTIVE SHEATH

This United States Non-Provisional Patent Application claims the benefit of U.S. Provisional Patent Application No. 61/913,939, filed Dec. 10, 2013, hereby incorporated by reference herein.

I. BACKGROUND OF THE INVENTION

A need exists for a protective sheath for use within a vaginal canal of a female user which conforms to the anatomy of the female genitalia.

II. SUMMARY OF THE INVENTION

A broad object of a particular embodiment of the invention can be to provide a protective sheath including a flexible tubular body having a body medial portion disposed between a body closed end portion and a body open end portion; and an annular flange extending radially outward from the body open end portion, the annular flange terminating in an annular flange edge having an elliptical annular flange edge perimeter.

Another broad object of a particular embodiment of the invention can be to provide a protective sheath further including a body closed end portion including a body closed end portion wall having a body closed end portion wall durometer which is greater than a body medial portion wall durometer of a body medial portion wall of the body medial portion.

Another broad object of a particular embodiment of the invention can be to provide a method of producing a protective sheath, the method including providing a flexible tubular body having a body medial portion disposed between a body closed end portion and a body open end portion; and extending an annular flange radially outward from the body open end portion; wherein the annular flange terminates in an annular flange edge having an elliptical annular flange edge perimeter.

Another broad object of a particular embodiment of the invention can be to provide a method of using a protective sheath within a vaginal canal of a user, the method including obtaining the protective sheath comprising: a flexible tubular body having a body medial portion disposed between a body closed end portion and a body open end portion; and an annular flange extending radially outward from the body open end portion, the annular flange terminating in an annular flange edge having an elliptical annular flange edge perimeter; inserting the body closed end portion into the vaginal canal toward a cervix of the female user; and engaging a portion of a vulva of the female user with the annular flange edge to preclude the annular flange edge from ingress into the vaginal canal.

Another broad object of a particular embodiment of the invention can be to provide a method of using a protective sheath within a vaginal canal of a user, the method further including stimulating the vulva of the female user with the annular flange edge.

Another broad object of a particular embodiment of the invention can be to provide a protective sheath including a flexible tubular body including a body medial portion having opposing body medial portion first and second open ends, the body medial portion second open end having a body medial portion second open end diameter; a discrete body end portion having opposing discrete body end portion open and closed ends, the discrete body end portion open end having a discrete body end portion open end diameter; whereby the discrete body end portion open end diameter is greater than the body medial portion second open end diameter; and whereby the discrete body end portion open end couples to the body medial portion second open end.

Another broad object of a particular embodiment of the invention can be to provide a method of producing a protective sheath, the method including providing a flexible tubular body comprising a body medial portion having opposing body medial portion first and second open ends, the body medial portion second open end having a body medial portion second open end diameter; and providing a discrete body end portion having opposing discrete body end portion open and closed ends, the discrete body end portion open end having a discrete body end portion open end diameter; whereby the discrete body end portion open end diameter is greater than the body medial portion second open end diameter; and coupling the discrete body end portion open end to the body medial portion second open end.

Naturally, further objects of the invention are disclosed throughout other areas of the specification, drawings, and claims.

III. BRIEF DESCRIPTION OF THE DRAWINGS

FIG. 2C is a bottom view of a particular embodiment of a protective sheath.

FIG. 2D is a first side view of a particular embodiment of a protective sheath.

FIG. 2E is a second side view of a particular embodiment of a protective sheath.

FIG. 2F is a closed end view of a particular embodiment of a protective sheath.

FIG. 2G is an open end view of a particular embodiment of a protective sheath.

FIG. 3C is a bottom view of a particular embodiment of a protective sheath.

FIG. 3D is a first side view of a particular embodiment of a protective sheath.

FIG. 4A is an enlarged open end view of a particular embodiment of a protective sheath detailing a bead element extending around an elliptical annular flange edge perimeter of an annular flange edge of an annular flange.

FIG. 4B is an enlarged open end view of a particular embodiment of a protective sheath detailing a bead element further including a texture element.

FIG. 5A is a cross-sectional view 5A-5A of the particular embodiment of the protective sheath shown in FIG. 2B.

FIG. 5B is a cross-sectional view 5B-5B of the particular embodiment of the protective sheath shown in FIG. 2B.

FIG. 5C is a cross-sectional view 5C-5C of the particular embodiment of the protective sheath shown in FIG. 3B.

FIG. 5D is a cross-sectional view 5D-5D of the particular embodiment of the protective sheath shown in FIG. 3B.

FIG. 8A is an illustration of a particular method of forming a bead element on a protective sheath, whereby the bead element has generally semi-circular cross section.

FIG. 8B is an enlarged view of the bead element having a generally semi-circular bead element cross section shown in FIG. 8A.

Figure 10A:
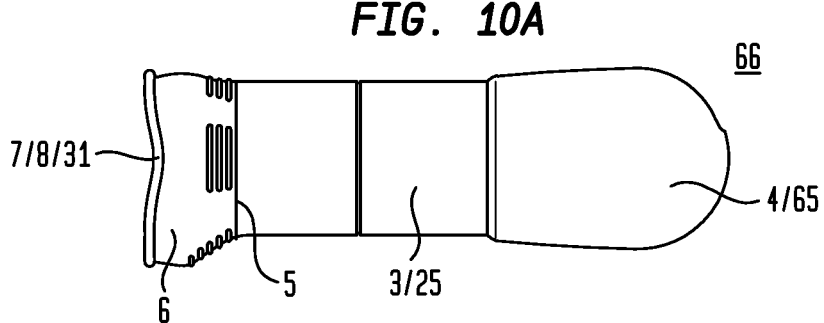
FIG. 10A is a view of a particular embodiment of a protective sheath having a collapsible body closed end portion in a body closed end portion deployed condition.
Figure 10B:
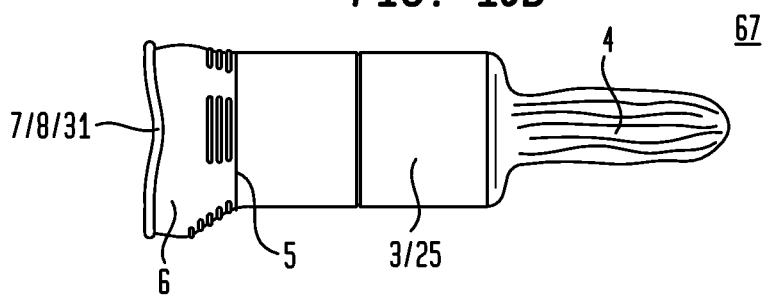
FIG. 10B is a view of a particular embodiment of a protective sheath having a collapsible body closed end portion in a body closed end portion collapsed condition.
Figure 10C:
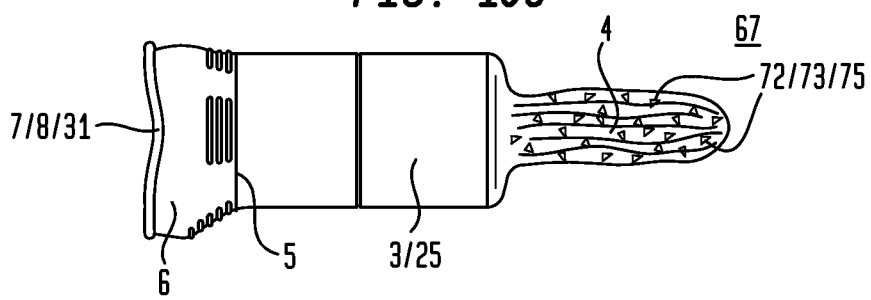
FIG. 10C is a view of a particular embodiment of a protective sheath having a collapsible body closed end portion in a body closed end portion collapsed condition, whereby the collapsible body closed end portion further includes a retention material configured as temperature-sensitive polyethylene glycol in a generally liquid polyethylene glycol condition.
Figure 10D:
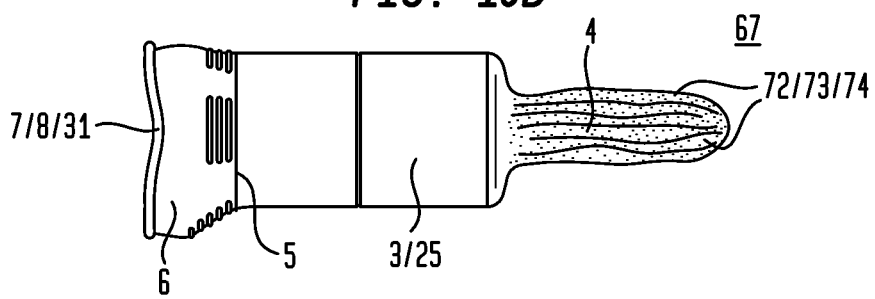
FIG. 10D is a view of a particular embodiment of a protective sheath having a collapsible body closed end portion in a body closed end portion collapsed condition, whereby the collapsible body closed end portion further includes a retention material configured as temperature-sensitive polyethylene glycol in a generally solid polyethylene glycol condition.
Figure 10E:
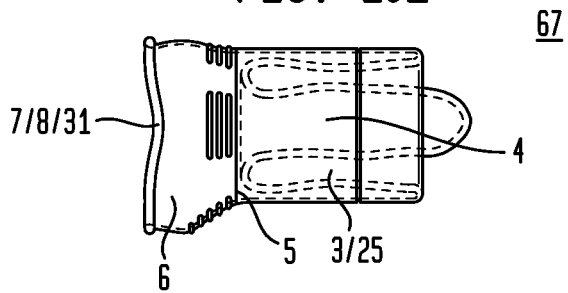

FIG. 10E is a view of a particular embodiment of a protective sheath having a collapsible body closed end portion in a body closed end portion collapsed condition within a flexible tubular body interior passage, whereby the collapsible body closed end portion further includes a retention material configured as temperature-sensitive polyethylene glycol in a generally solid polyethylene glycol condition.

Figure 11A:
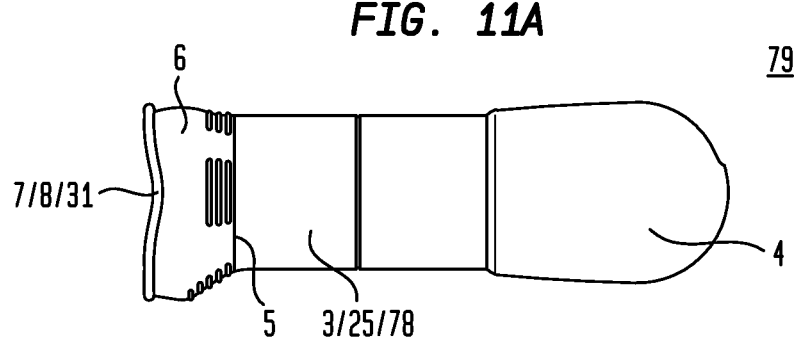

FIG. 11A is a view of a particular embodiment of a protective sheath.

Figure 11B:
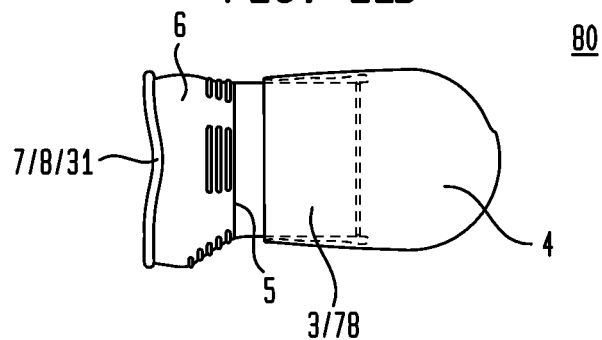

FIG. 11B is a view of a particular embodiment of a protective sheath having a body medial portion telescopingly engaged within a body closed end portion interior space.

Figure 12A:
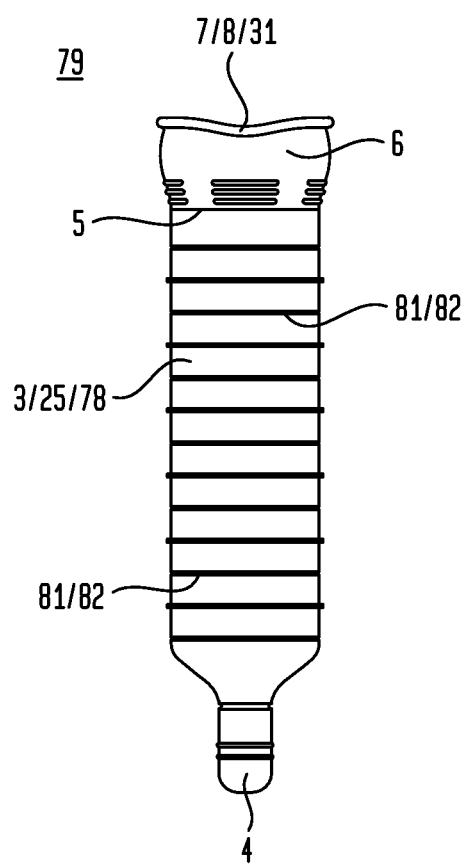

FIG. 12A is a view of a particular embodiment of a protective sheath having a collapsible body medial portion in a body medial portion deployed condition.

Figure 12B:
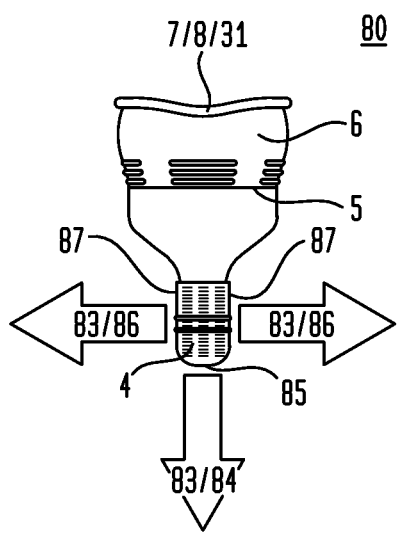

FIG. 12B is a view of a particular embodiment of a protective sheath having a collapsible body medial portion in a body medial portion collapsed condition within a body closed end portion interior space.

FIG. 13A is a view of a former used to form a particular embodiment of a protective sheath.

FIG. 13B is a cross-sectional view a first, second, third, and fourth coating on a former used to form a particular embodiment of a protective sheath.

FIG. 14A is a view of a former used to form a particular embodiment of a protective sheath.

FIG. 14B is a cross-sectional view of a first, second, third, and fourth coating on a former used to form a particular embodiment of a protective sheath.

Figure 15:
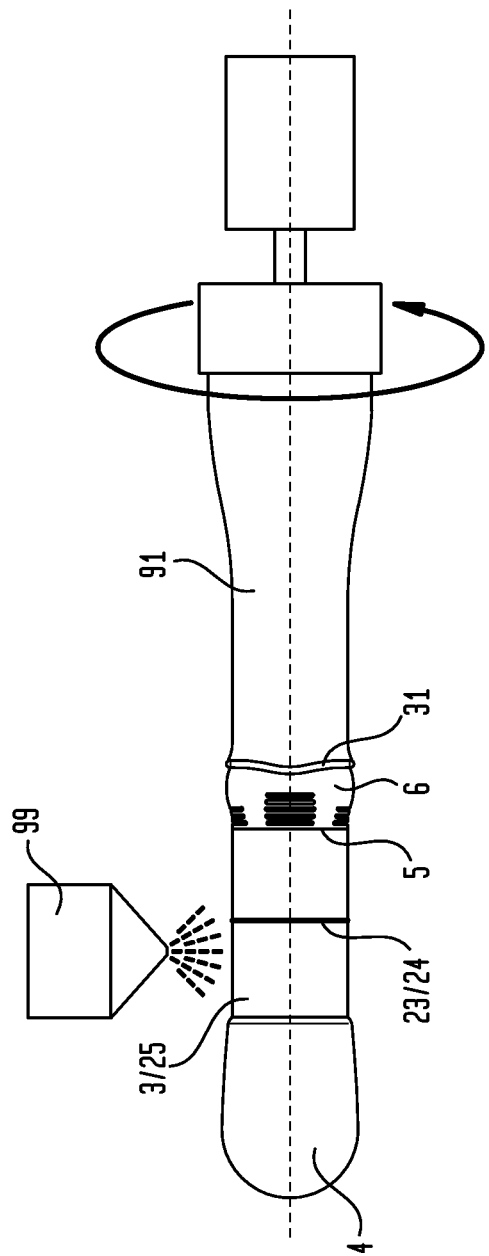

FIG. 15 is an illustration of a particular method of producing a first, second, third, and fourth coating on a former to form a particular embodiment of a protective sheath.

Figure 16:
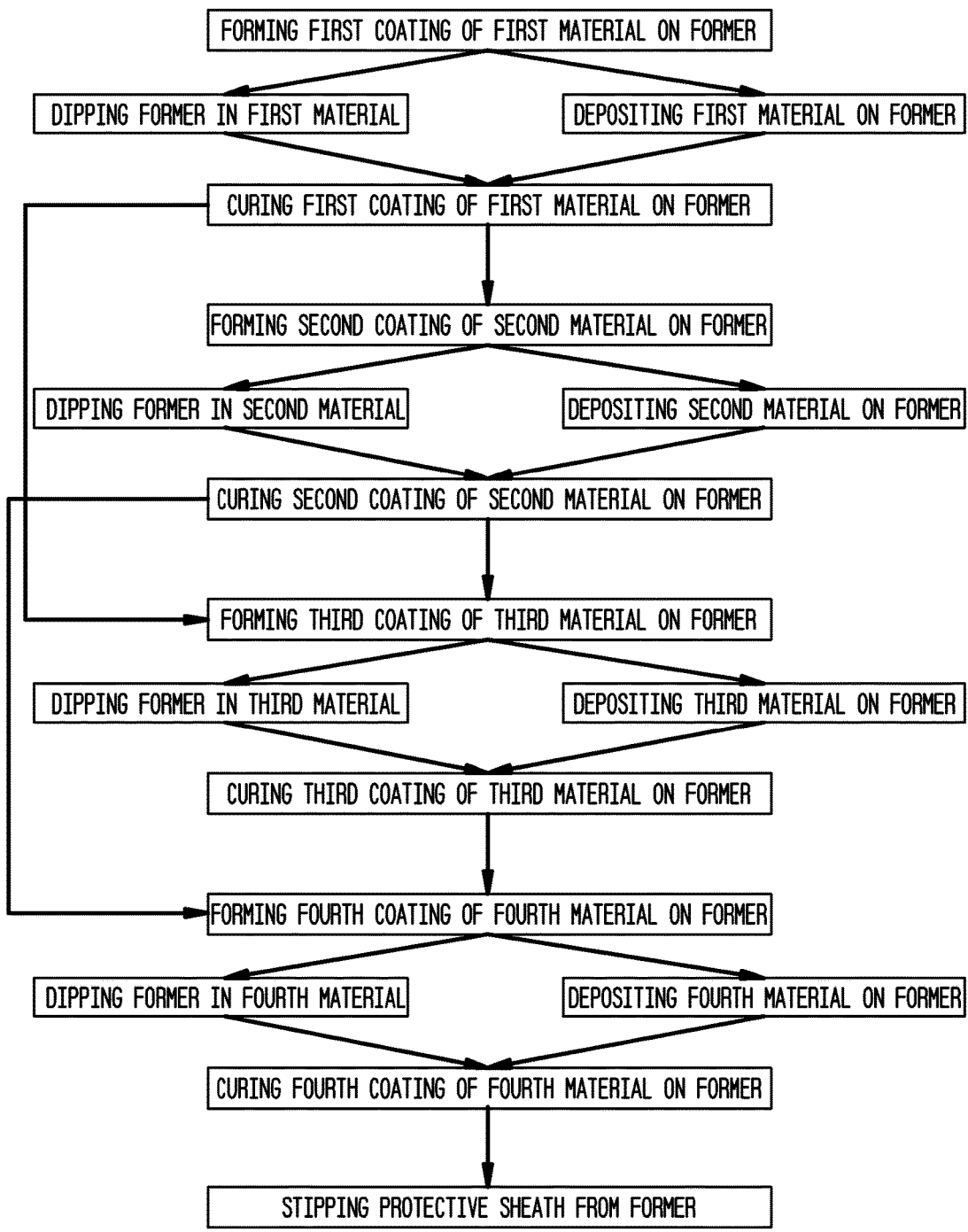

FIG. 16 provides a flow chart illustrating a particular method of producing a protective sheath.

Figure 17:
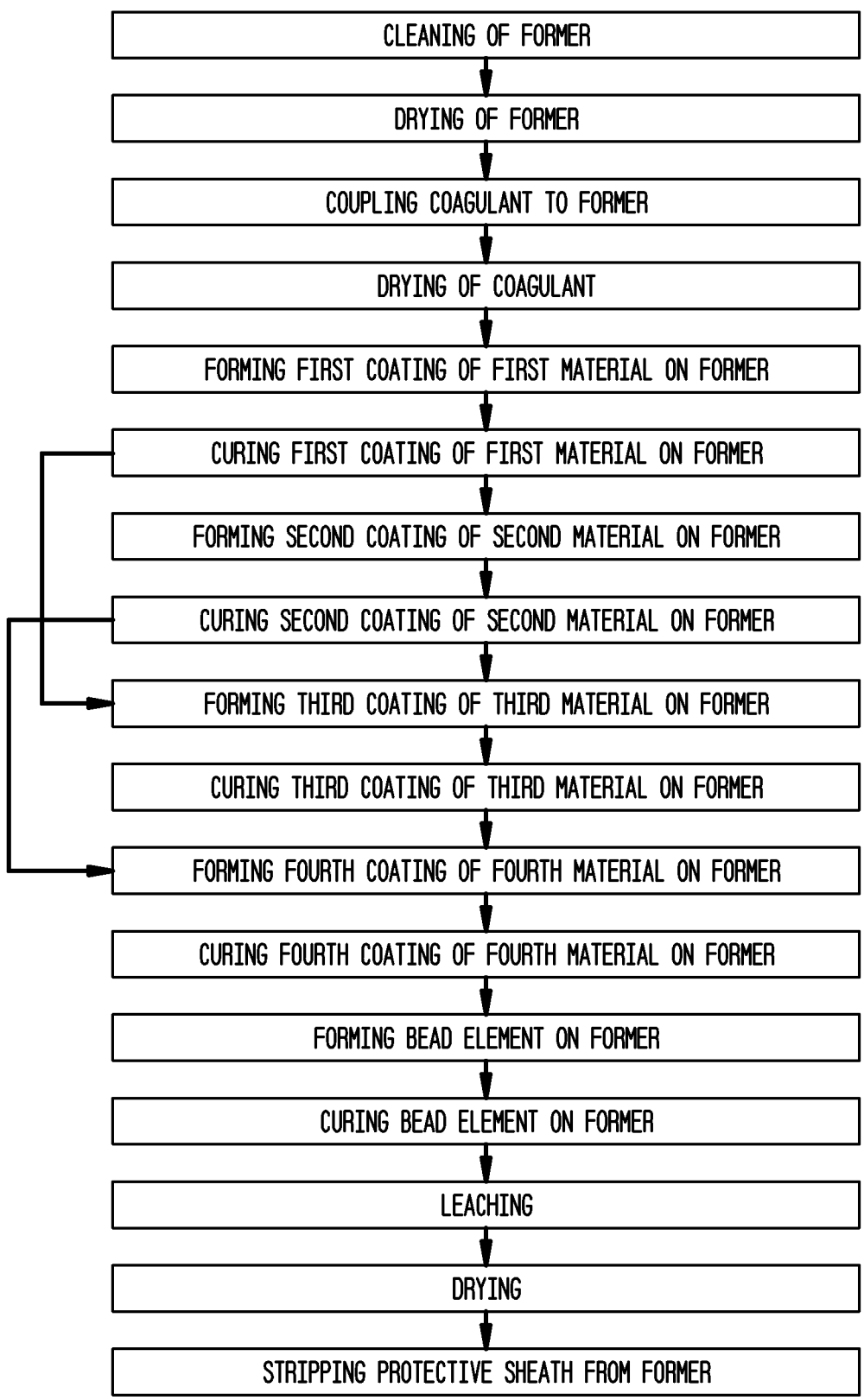

FIG. 17 provides a flow chart illustrating a particular method of producing a protective sheath.

FIG. 18 is an illustration of a particular method of producing a protective sheath from a plurality of discrete pieces.

FIG. 19A is a view of a particular embodiment of a protective sheath.

FIG. 19B is an enlarged view of a portion of the particular embodiment of the protective sheath shown in FIG. 19A.

IV. DETAILED DESCRIPTION OF THE INVENTION

Figure 1A:
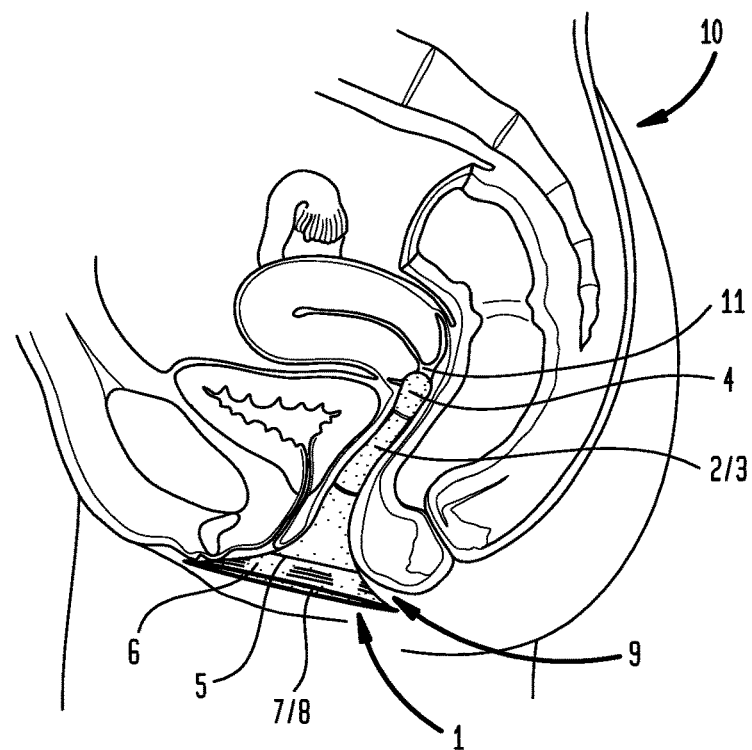
FIG. 1A is an illustration of a particular method of using a protective sheath.
Figure 1B:
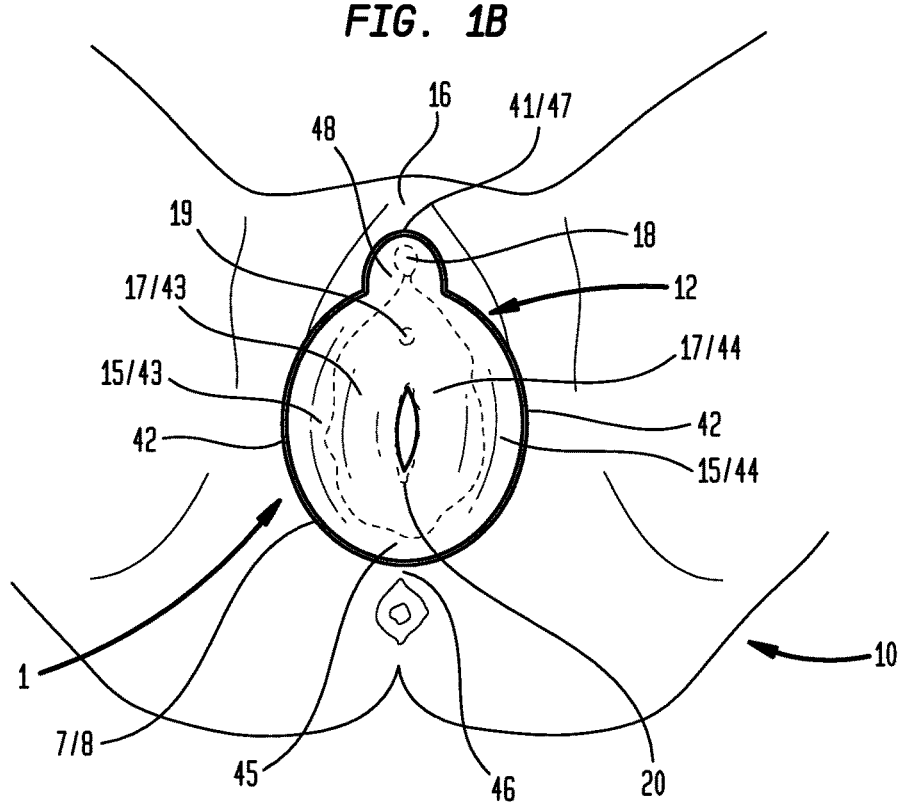
FIG. 1B is an illustration of a particular method of using a protective sheath.
Figure 2A:
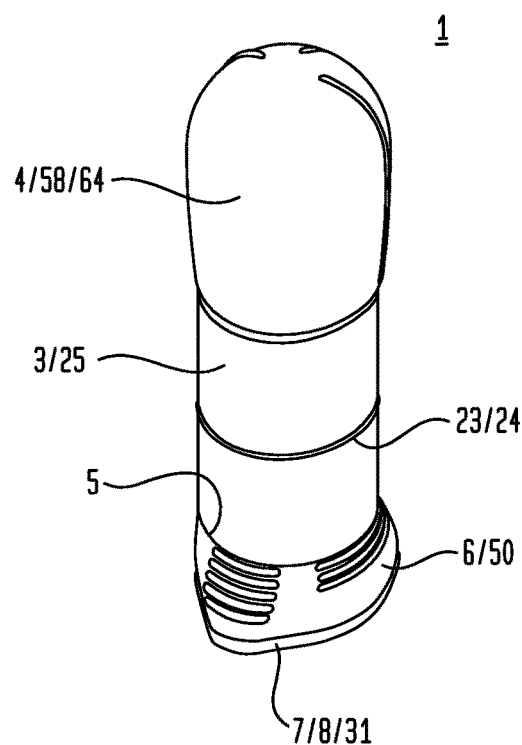
FIG. 2A is a perspective view of a particular embodiment of a protective sheath.
Figure 2B:
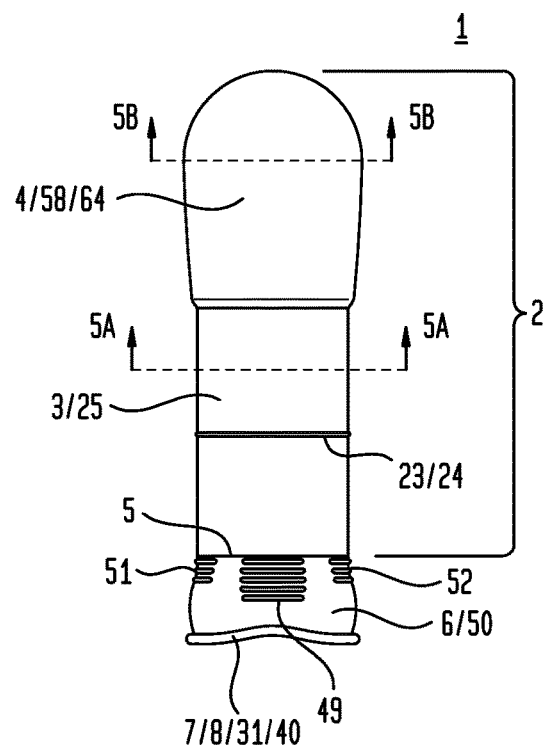
FIG. 2B is a top view of a particular embodiment of a protective sheath.

Now referring primarily to FIG. 1A and FIG. 1B, which illustrate a method of using a protective sheath (1) including a flexible tubular body (2) having a body medial portion (3) disposed between a body closed end portion (4) and a body open end portion (5). The protective sheath (1) further includes an annular flange (6) extending radially outward from the body open end portion (5), whereby the annular flange (6) terminates in an annular flange edge (7) an elliptical annular flange edge perimeter (8). As to particular embodiments, the method of using the protective sheath (1) within a vaginal canal (9) of a female user (10) can include inserting the body closed end portion (4) into the vaginal canal (9) toward a cervix (11) and engaging a portion of a vulva (12) of the female user (10) with the annular flange edge (7) to preclude the annular flange edge (7) from ingress into the vaginal canal (9). During coitus, the protective sheath (1) can function to prevent conception, disease transmission, or the like, or combinations thereof.

The term "protective sheath" for the purposes of the present invention means a mechanical barrier intended for insertion into the vaginal canal (9) of a female user (10) to prevent or protect the female user (10) from conception during coitus; to prevent or protect the female user (10) from disease transmission, for example during coitus; to prevent or protect a male partner from disease transmission during coitus; or the like; or combinations thereof.

The term "elliptical" for the purposes of the present invention means having a configuration generally relating to an ellipse, an oval, an elongate circle, or the like, whereby the elliptical configuration has an arcuate circumference and substantially perpendicular major and minor diameters (13) (14), whereby the major diameter (13) is greater than the minor diameter (14) (as shown in the example of FIG. 4A). The term "elliptical" as used herein is intended to be broader than the mathematical definition, which defines an ellipse as a curve on a plane surrounding two focal points such that a straight line drawn from one of the focal points to any point on the curve and then back to the other focal point has the same length for every point on the curve.

The term "vulva" for the purposes of the present invention means the external genitalia of a female, including the labia majora (15), mons pubis (16), labia minora (17), clitoris (18), bulb of vestibule, vulval vestibule, greater and lesser vestibular glands, external urethral orifice (19), and the opening of the vagina (introitus) (20) (as shown in the example of FIG. 1B).

Now referring primarily to FIG. 2A through FIG. 3G, the protective sheath (1) includes a flexible tubular body (2) having a body medial portion (3) disposed between a body closed end portion (4) and a body open end portion (5). The flexible tubular body (2) can be formed from any of a numerous and wide variety of materials capable of providing a mechanical barrier between a vaginal canal (9) of a female user (10) and an object inserted into the vaginal canal (9), for example a penis of a male partner which may be inserted into the vaginal canal (9) during coitus. As non-limiting examples, materials which may be useful for forming particular embodiments of the flexible tubular body (2) can include polymeric materials, natural rubber latex, acrylonitrile butadiene rubber, polyisoprene latex, polyvinyl chloride, polychloroprene rubber, polyurethane, or the like, or combinations thereof.

Now referring primarily to FIG. 2A through FIG. 3G, FIG. 13A through FIG. 14B, and FIG. 18, the body medial portion (3) of the flexible tubular body (2) can include a generally constant diameter between the body closed end portion (4) and the body open end portion (5). Additionally, now referring primarily to FIG. 2B, FIG. 3B, and FIG. 5, the body medial portion (3) of the flexible tubular body (2) can include a body medial portion wall (21) having a body medial portion wall thickness (22), which can be in a range of between about 0.03 millimeters to about 0.8 millimeters. As to particular embodiments, the body medial portion wall thickness (22) can be in a range selected from the group including or consisting of: between about 0.03 millimeters to about 0.1 millimeters; between about 0.05 millimeters to about 0.15 millimeters; between about 0.1 millimeters to about 0.2 millimeters; between about 0.15 millimeters to about 0.25 millimeters; between about 0.2 millimeters to about 0.3 millimeters; between about 0.25 millimeters to about 0.35 millimeters; between about 0.3 millimeters to about 0.4 millimeters; between about 0.35 millimeters to about 0.45 millimeters; between about 0.4 millimeters to about 0.5 millimeters; between about 0.45 millimeters to about 0.55 millimeters; between about 0.5 millimeters to about 0.6 millimeters; between about 0.55 millimeters to about 0.65 millimeters; between about 0.6 millimeters to about 0.7 millimeters; between about 0.65 millimeters to about 0.75 millimeters; and between about 0.7 millimeters to about 0.8 millimeters.

Now referring primarily to FIG. 2A through FIG. 3G, the body medial portion (3) can further include at least one body medial portion retention element (23), which can facilitate retention of the body medial portion (3) within the vaginal canal (9) of the female user (10), particularly during coitus. As an illustrative example, the body medial portion retention element (23) can be configured as a body medial portion circumferential protrusion (24) which outwardly extends from a body medial portion outer surface (25) of the body medial portion (3).

Now referring primarily to FIG. 2A through FIG. 4B, the protective sheath (1) further includes an annular flange (6) extending radially outward from the body open end portion (5). The annular flange (6) terminates in an annular flange edge (7) having an elliptical annular flange edge perimeter (8).

As to particular embodiments, the annular flange (6) can further include an annular flange wall (26) having an annular flange wall durometer (27) which is greater than a body medial portion wall durometer (28) of the body medial portion wall (21) of the body medial portion (3). Hence, the greater annular flange wall durometer (27) can provide greater strength, rigidity, or the like, or combinations thereof, to the annular flange wall (26) relative to the body medial portion wall (21).

As to particular embodiments, the annular flange (6) can further include an annular flange wall (26) having an annular flange wall thickness (29) which is greater than the body medial portion wall thickness (22). Hence, the greater annular flange wall thickness (29) can provide greater strength, rigidity, or the like, or combinations thereof, to the annular flange wall (26) relative to the body medial portion wall (21).

As to particular embodiments having an annular flange wall (26) with an annular flange wall thickness (29) which is greater than the body medial portion wall thickness (22), the annular flange wall thickness (29) can be in a range of between about 0.1 millimeters to about 1.5 millimeters. As to particular embodiments, the annular flange wall thickness (29) can be in a range selected from the group including or consisting of: between about 0.1 millimeters to about 0.5 millimeters; between about 0.25 millimeters to about 0.75 millimeters; between about 0.5 millimeters to about 1 millimeter; between about 0.75 millimeters to about 1.25 millimeters; and between about 1 millimeter to about 1.5 millimeters; whereby a greater annular flange wall thickness (29) provides greater strength, rigidity, or the like, or combinations thereof, to the annular flange wall (26).

Now referring primarily to FIG. 4A, the elliptical annular flange edge perimeter (8) can be configured as an ellipse, an oval, an elongate circle, or the like, whereby the elliptical configuration has an arcuate circumference and substantially perpendicular major and minor diameters (13)(14), whereby the major diameter (13) is greater than the minor diameter (14). In contrast, a circle has substantially equivalent major and minor diameters.

Figure 3A:
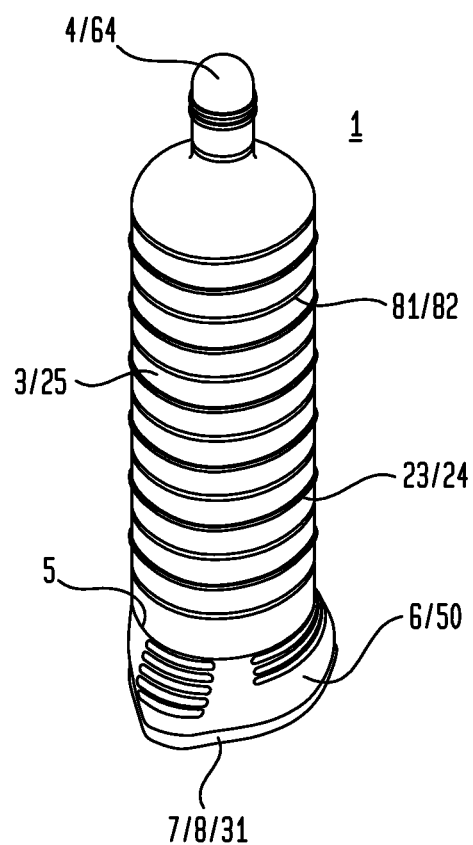
FIG. 3A is a perspective view of a particular embodiment of a protective sheath.
Figure 3B:
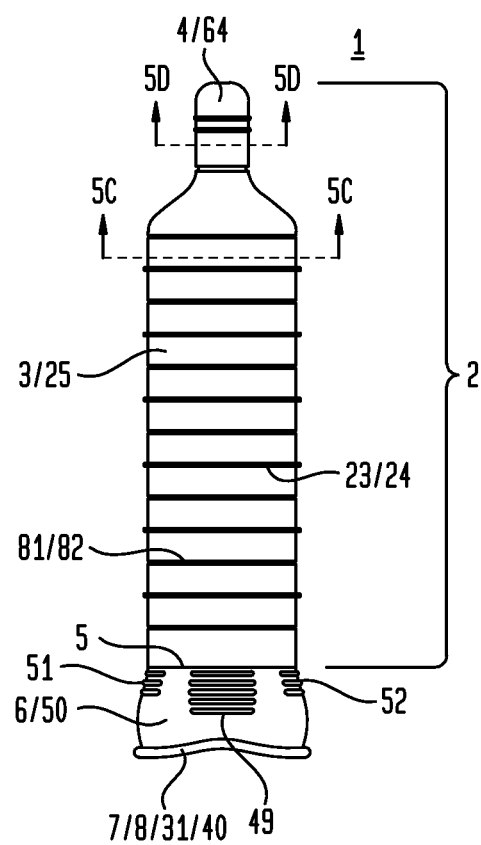
FIG. 3B is a top view of a particular embodiment of a protective sheath.
Figure 3E:
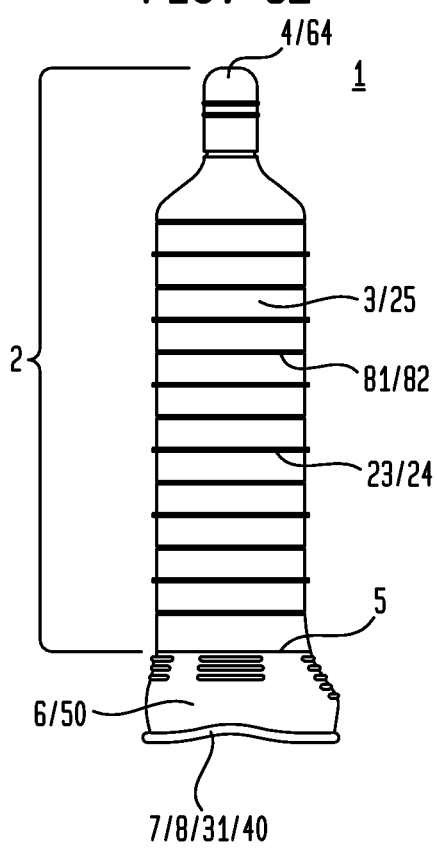
FIG. 3E is a second side view of a particular embodiment of a protective sheath.
Figure 3F:
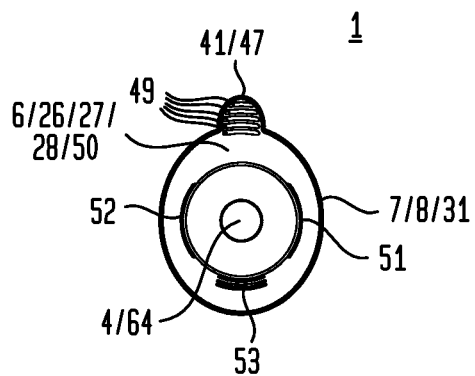
FIG. 3F is a closed end view of a particular embodiment of a protective sheath.
Figure 3G:
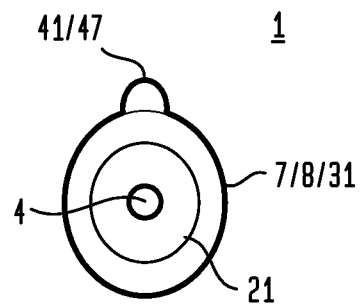
FIG. 3G is an open end view of a particular embodiment of a protective sheath.

Now referring primarily to FIG. 2G and FIG. 3G, the elliptical annular flange edge perimeter (8) can be greater than a body medial portion perimeter (30) of the body medial portion (3). Accordingly, the dimensional relations of the elliptical annular flange edge perimeter (8) can be sufficient to preclude the annular flange edge (7) from ingress into the vaginal canal (9) of the female user (10) following insertion of the body closed end portion (4) of the flexible tubular body (2) into the vaginal canal (9) of the female user (10), particularly during coitus.

Now referring primarily to FIG. 1B, when the protective sheath (1) is used by a female user (10), the annular flange edge (7) having the elliptical annular flange edge perimeter (8) can be configured to overlay a portion of a vulva (12) which is bounded by a generally elliptical vulva perimeter. Correspondingly, the elliptical annular flange edge perimeter (8) can be contoured to extend in generally adjacent parallel relation to the generally elliptical vulva perimeter. As to particular embodiments, the elliptical annular flange edge perimeter (8) contoured to extend in generally adjacent parallel relation to the generally elliptical vulva perimeter can facilitate stimulation of the vulva (12), particularly during coitus.

Figure 6C:
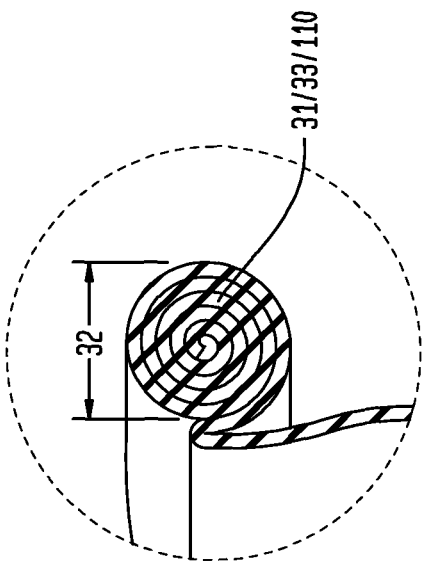
FIG. 6C is an enlarged view of the bead element having a generally circular bead element cross section shown in FIG. 6B.
Figure 7A:
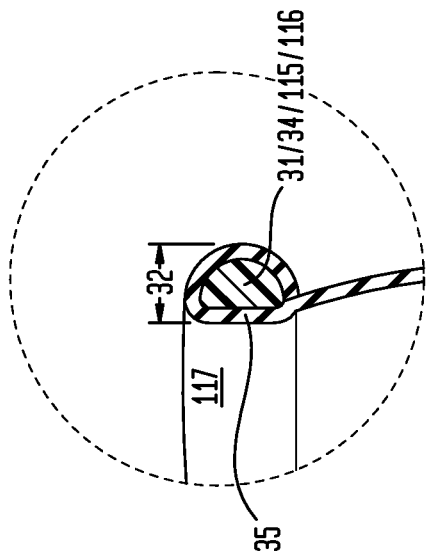
FIG. 7A is an illustration of a particular method of forming a bead element on a protective sheath, whereby the bead element has generally semi-circular cross section.
Figure 7B:
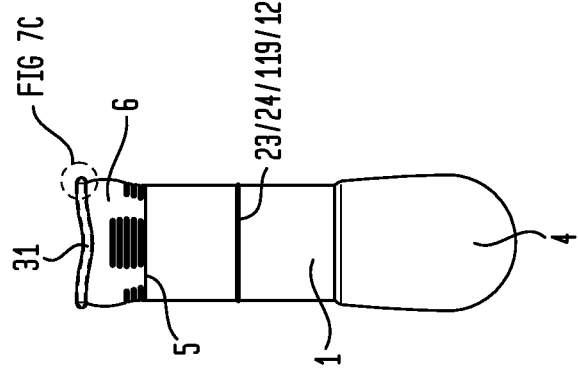
FIG. 7B is a view of a particular embodiment of a protective sheath including a bead element having a generally semi-circular bead element cross section.
Figure 7C:
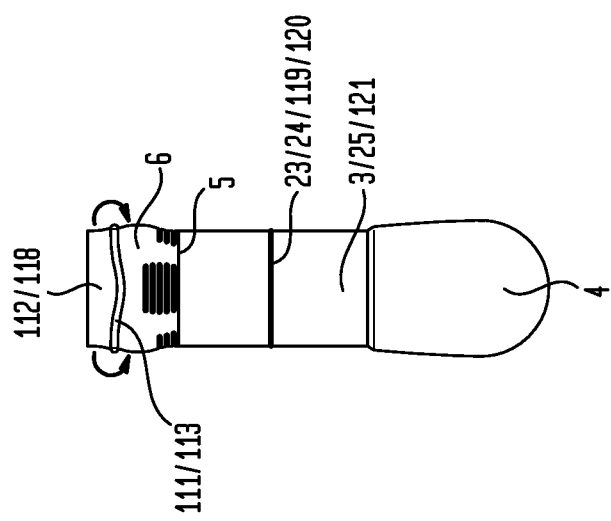
FIG. 7C is an enlarged view of the bead element having a generally semi-circular bead element cross section shown in FIG. 7B.

Now referring primarily to FIG. 6C, FIG. 7C, and FIG. 8B, the annular flange edge (7) can further include a bead element (31) extending around the elliptical annular flange edge perimeter (8), whereby the bead element (31) can function to reinforce the annular flange edge (7). As an illustrative example, the bead element (31) can have a bead element thickness (32) which is greater than the body medial portion wall thickness (22). Hence, the greater bead element thickness (32) can provide greater strength, rigidity, or the like, or combinations thereof, to the bead element (31) relative to the body medial portion wall (21).

The bead element thickness (32) can be in a range of between about 0.1 millimeters to about 3 millimeters. As to particular embodiments, the bead element thickness (32) can be in a range selected from the group including or consisting of: between about 0.1 millimeters to about 0.5 millimeters; between about 0.25 millimeters to about 0.75 millimeters; between about 0.5 millimeters to about 1 millimeter; between about 0.75 millimeters to about 1.25 millimeters; between about 1 millimeter to about 1.5 millimeters; between about 1.25 millimeters to about 1.75 millimeters; between about 1.5 millimeters to about 2 millimeters; between about 1.75 millimeters to about 2.25 millimeters; between about 2 millimeters to about 2.5 millimeters; between about 2.25 millimeters to about 2.75 millimeters; and between about 2.5 millimeters to about 3 millimeters; whereby a greater bead element thickness (32) provides greater strength, rigidity, or the like, or combinations thereof, to the bead element (31).

Now referring primarily to FIG. 6C, as to particular embodiments, the bead element (31) can have a generally circular bead element cross section (33).

Now referring primarily to FIG. 7C and FIG. 8B, as to other particular embodiments, the bead element (31) can have a generally semi-circular bead element cross section (34), whereby a generally planar bead element portion (35) of the bead element (31) having the generally semi-circular bead element cross section (34) can dispose proximate an annular flange opening (36) bounded by the annular flange edge (7). As to particular embodiments, the generally planar bead element portion (35) can increase the rolling resistance of the bead element (31) having the generally semi-circular bead element cross section (34) in relation to the bead element (31) having the generally circular bead element cross section (33), which may have a greater tendency to roll upon itself toward the body closed end portion (4).

Now referring primarily to FIG. 4B, the bead element (31) can further include a texture element (37) coupled to the bead element (31), for example to a bead element outer surface (38) of the bead element (31). As to particular embodiments, the texture element (37) can be configured as a plurality of texture element protrusions (39) which can facilitate stimulation of the vulva (12) of the female user (10), particularly during coitus.

Now referring primarily to FIG. 2A through FIG. 3G, the bead element (31) can further include a non-planar bead element perimeter (40). As an illustrative example, when the protective sheath (1) is used by a female user (10), a clitoral bead element portion (41) which disposes proximate the clitoris (18) of the female user (10) can be a lesser distance from the body closed end portion (4) relative to a labial bead element portion (42) which disposes proximate a right or left labial portion (43)(44) of the female user (10). As an additional illustrative example, when the protective sheath (1) is used by a female user (10), a perineum bead element portion (45) which disposes proximate a portion of a perineum (46) of the female user (10) can be a lesser distance from the body closed end portion (4) relative to the labial bead element portion (42) which disposes proximate the right or left labial portion (43)(44) of the female user (10).

Now referring primarily to FIG. 2A through FIG. 4B, the annular flange edge (7) can further include an arcuate element (47) extending radially outward from the elliptical annular flange edge perimeter (8). An annular flange portion (48) proximate the arcuate element (47) can be configured to engage the clitoris (18) of the female user (10) when the protective sheath (1) is used by the female user (10).

Now referring primarily to FIG. 2A through FIG. 3G, as to particular embodiments, the annular flange (6) can further include a first protrusion (49) outwardly extending from an annular flange outer surface (50). The first protrusion (49) can be configured to engage the clitoris (18) of the female user (10) when the protective sheath (1) is used by the female user (10), which can facilitate stimulation of the clitoris (18), particularly during coitus. As to particular embodiments, the first protrusion (49) can include a plurality of generally linear first protrusions (49) circumferentially extending across a portion of the annular flange outer surface (50). However, the invention need not be so limited, as the first protrusion (49) can have any of a numerous and wide variety of configurations of varying dimensions, such as generally circular protrusions, generally elliptical protrusions, generally polygonal protrusions, generally linear protrusions, arcuate protrusions, or the like, or combinations thereof.

Again referring primarily to FIG. 2A through FIG. 3G, as to particular embodiments, the annular flange (6) can further include a second protrusion (51) outwardly extending from the annular flange outer surface (50). The second protrusion (51) can be configured to engage the right labial portion (43) of the vulva (12) of the female user (10) when the protective sheath (1) is used by the female user (10), which can facilitate stimulation of the right labial portion (43), particularly during coitus. As to particular embodiments, the second protrusion (51) can include a plurality of generally linear second protrusions (51) circumferentially extending across a portion of the annular flange outer surface (50). However, the invention need not be so limited, as the second protrusion (51) can have any of a numerous and wide variety of configurations of varying dimensions, such as generally circular protrusions, generally elliptical protrusions, generally polygonal protrusions, generally linear protrusions, arcuate protrusions, or the like, or combinations thereof.

Again referring primarily to FIG. 2A through FIG. 3G, as to particular embodiments, the annular flange (6) can further include a third protrusion (52) outwardly extending from the annular flange outer surface (50). The third protrusion (52) can be configured to engage the left labial portion (44) of the vulva (12) of the female user (10) when the protective sheath (1) is used by the female user (10), which can facilitate stimulation of the left labial portion (44), particularly during coitus. As to particular embodiments, the third protrusion (52) can include a plurality of generally linear third protrusions (52) circumferentially extending across a portion of the annular flange outer surface (50). However, the invention need not be so limited, as the third protrusion (52) can have any of a numerous and wide variety of configurations of varying dimensions, such as generally circular protrusions, generally elliptical protrusions, generally polygonal protrusions, generally linear protrusions, arcuate protrusions, or the like, or combinations thereof.

Again referring primarily to FIG. 2A through FIG. 3G, as to particular embodiments, the annular flange (6) can further include a fourth protrusion (53) outwardly extending from the annular flange outer surface (50). The fourth protrusion (53) can be configured to engage a portion of the perineum (46) of the female user (10) when the protective sheath (1) is used by the female user (10), which can facilitate stimulation of the portion of the perineum (46), particularly during coitus. As to particular embodiments, the fourth protrusion (53) can include a plurality of generally linear fourth protrusions (53) circumferentially extending across a portion of the annular flange outer surface (50). However, the invention need not be so limited, as the fourth protrusion (53) can have any of a numerous and wide variety of configurations of varying dimensions, such as generally circular protrusions, generally elliptical protrusions, generally polygonal protrusions, generally linear protrusions, arcuate protrusions, or the like, or combinations thereof.

Again referring primarily to FIG. 2A through FIG. 3G, as to particular embodiments, the flexible tubular body (2) of the protective sheath (1) can further include a body closed end portion (4) having a body closed end portion wall (54) with a body closed end portion wall durometer (55) which is greater than a body medial portion wall durometer (28) of the body medial portion wall (21) of the body medial portion (3). Hence, the greater body closed end portion wall durometer (55) can provide greater strength, rigidity, or the like, or combinations thereof, to the body closed end portion wall (54) relative to the body medial portion wall (21).

Now referring primarily to FIG. 2A through FIG. 3G and FIG. 5A and FIG. 5B, as to particular embodiments, the flexible tubular body (2) of the protective sheath (1) can further include a body closed end portion (4) having a body closed end portion wall (54) with a body closed end portion wall thickness (56) which is greater than the body medial portion wall thickness (22). Hence, the greater body closed end portion wall thickness (56) can provide greater strength, rigidity, or the like, or combinations thereof, to the body closed end portion wall (54) relative to the body medial portion wall (21).

The body closed end portion wall thickness (56) can be in a range of between about 0.1 millimeters to about 1.5 millimeters. As to particular embodiments, the body closed end portion wall thickness (56) can be in a range selected from the group including or consisting of: between about 0.1 millimeters to about 0.5 millimeters; between about 0.25 millimeters to about 0.75 millimeters; between about 0.5 millimeters to about 1 millimeter; between about 0.75 millimeters to about 1.25 millimeters; and between about 1 millimeter to about 1.5 millimeters; whereby a greater body closed end portion wall thickness (56) provides greater strength, rigidity, or the like, or combinations thereof, to the body closed end portion wall (54).

Now referring primarily to FIG. 2A through FIG. 2G and FIG. 5A, as to particular embodiments, the body closed end portion (4) can further include a body closed end portion perimeter (57) which is greater than the body medial portion perimeter (30). As to particular embodiments, the greater body closed end portion perimeter (57) can facilitate retention of the body closed end portion (4) within the vaginal canal (9) proximate the cervix (11) of a female user (10), particularly during coitus.

Now referring primarily to FIG. 2A through FIG. 2G, as an illustrative example, a body closed end portion (4) having a body closed end portion perimeter (57) which is greater than the body medial portion perimeter (30) can be configured as bulbous body closed end portion (58).

Now referring primarily to FIG. 3A through FIG. 3G and FIG. 5B, as to other particular embodiments, the body closed end portion (4) can further include a body closed end portion perimeter (57) which is lesser than the body medial portion perimeter (30). As to these particular embodiments, because the generally elliptical annular flange edge perimeter (8) is greater than a body medial portion perimeter (30) of the body medial portion (3), as described above, and the body closed end portion perimeter (57) is lesser than the body medial portion perimeter (30), as described above, then regarding the protective sheath as a whole, it necessarily flows that the generally elliptical annular flange edge perimeter defines the largest circumference about a longitudinal axis of the protective sheath and the body closed end portion perimeter provides the smallest circumference about the longitudinal axis of the protective sheath, as shown in FIG. 3A through FIG. 3G.

Now referring primarily to FIG. 2A through FIG. 3G, the body closed end portion (4) can further include at least one body closed end portion retention element (59), which can facilitate retention of the body closed end portion (4) within the vaginal canal (9) proximate the cervix (11) of the female user (10), particularly during coitus. As an illustrative example, the body closed end portion retention element (59) can be configured as a body closed end portion protrusion (60), for example a body closed end portion longitudinal protrusion (61) or body closed end portion circumferential protrusion (62), which outwardly extends from a body closed end portion outer surface (64) of the body closed end portion (4).

Now referring primarily to FIG. 9A through FIG. 10E, as to particular embodiments, the body closed end portion (4) can be configured as a collapsible body closed end portion (65), which can collapse from a body closed end portion deployed condition (66) toward a body closed end portion collapsed condition (67), in which the collapsible body closed end portion (65) occupies a lesser volume of space in relation to the body closed end portion deployed condition (66).

Figure 9A:
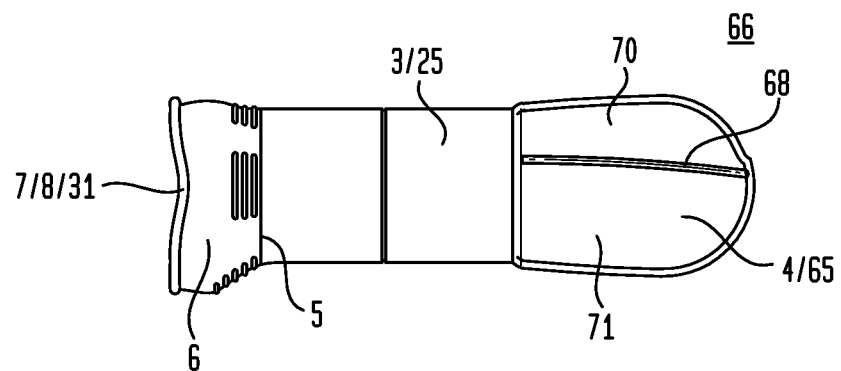
FIG. 9A is a view of a particular embodiment of a protective sheath having a collapsible body closed end portion in a body closed end portion deployed condition.
Figure 9B:
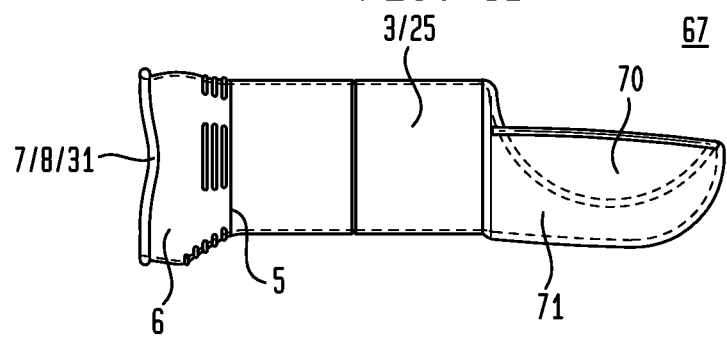
FIG. 9B is a view of a particular embodiment of a protective sheath having a collapsible body closed end portion in a body closed end portion collapsed condition.
Figure 9C:
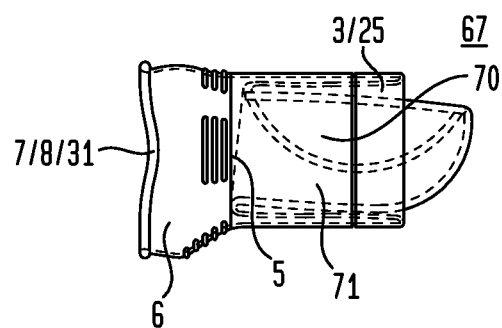
FIG. 9C is a view of a particular embodiment of a protective sheath having a collapsible body closed end portion in a body closed end portion collapsed condition within a flexible tubular body interior passage.

Now referring primarily to FIG. 9A through FIG. 9C, as to particular embodiments, the collapsible body closed end portion (65) can further include at least one collapsible body closed end portion recess (68) which can facilitate collapsing of the collapsible body closed end portion (65) from the body closed end portion deployed condition (66) toward the body closed end portion collapsed condition (67).

Again referring primarily to FIG. 9A through FIG. 9C, as to particular embodiments, the collapsible body closed end portion recess (68) can be disposed along a collapsible body closed end portion longitudinal axis, thereby dividing the collapsible body closed end portion (65) into collapsible body closed end portion first and second longitudinal halves (70)(71). To achieve the body closed end portion collapsed condition (67), the collapsible body closed end portion (65) can be folded along the collapsible body closed end portion recess (68) disposed along the collapsible body closed end portion longitudinal axis to fold the collapsible body closed end portion first longitudinal half (70) within the collapsible body closed end portion second longitudinal half (71).

Now referring primarily to FIG. 10A through FIG. 10E, as to particular embodiments, the collapsible body closed end portion (65) can further include a retention material (72) which can retain the collapsible body closed end portion (65) in the body closed end portion collapsed condition (67) until deployment into the body closed end portion deployed condition (66). As a non-limiting example, the retention material (72) can be configured as temperature-sensitive polyethylene glycol (PEG) (73) having properties whereby the temperature-sensitive polyethylene glycol (73) is in a generally solid polyethylene glycol condition (74) at temperatures lesser than the vaginal canal temperature and the temperature-sensitive polyethylene glycol (73) is in a generally liquid polyethylene glycol condition (75) at temperatures equal to or greater than the vaginal canal temperature.

Again referring primarily to FIG. 10A through FIG. 10E, as an illustrative example, the temperature-sensitive polyethylene glycol (73) in the generally liquid polyethylene glycol condition (75) can be coupled to the collapsible body closed end portion (65) in the body closed end portion collapsed condition (67) (for example by coating the collapsible body closed end portion (65) in the body closed end portion collapsed condition (67) with the temperature-sensitive polyethylene glycol (73) in the generally liquid polyethylene glycol condition (75)), whereby upon a decrease in temperature, the temperature-sensitive polyethylene glycol (73) in the generally liquid polyethylene glycol condition (75) can solidify into the generally solid polyethylene glycol condition (74). Accordingly, the temperature-sensitive polyethylene glycol (73) in the generally solid polyethylene glycol condition (74) can function to retain the collapsible body closed end portion (65) in the body closed end portion collapsed condition (67). Upon insertion of the collapsible body closed end portion (65) retained in the body closed end portion collapsed condition (67) by the temperature-sensitive polyethylene glycol (73) in the generally solid polyethylene glycol condition (66) into the vaginal canal (9) of the female user (10), the temperature-sensitive polyethylene glycol (73) in the generally solid polyethylene glycol condition (74) can be exposed to the vaginal canal temperature, whereby the temperature-sensitive polyethylene glycol (73) in the generally solid polyethylene glycol condition (74) can liquefy into the generally liquid polyethylene glycol condition (75), thereby allowing deployment of the collapsible body closed end portion (65) from the body closed end portion collapsed condition (67) toward the body closed end portion deployed condition (66) within the vaginal canal (9) of the female user (10).

As to particular embodiments, the body closed end portion collapsed condition (67) can facilitate actuation of the collapsible body closed end portion (65) toward the body closed end portion deployed condition (66) when the collapsible body closed end portion (65) is inserted into the vaginal canal (9) toward a cervix (11) of a female user (10).

Now referring primarily to FIG. 9A through FIG. 10E, as to particular embodiments, the body closed end (4) or the collapsible body closed end (65) in the body closed end collapsed condition (67) can be disposed within a flexible tubular body interior passage (76) bounded by the body medial portion wall (21) toward the body open end portion (5) to reduce a flexible tubular body volume of the flexible tubular body (2).

Now referring primarily to FIG. 11A and FIG. 11B, as to other particular embodiments, the body medial portion (3) can telescopingly engage within a body closed end portion interior space (77) bounded by the body closed end portion wall (54) to reduce the flexible tubular body volume of the flexible tubular body (2).

Now referring primarily to FIG. 12A and FIG. 12B, as to particular embodiments, the flexible tubular body (2) can further include a body medial portion (3) configured as a collapsible body medial portion (78), which can collapse from a body medial portion deployed condition (79) toward a body medial portion collapsed condition (80), in which the collapsible body medial portion (78) occupies a lesser volume of space in relation to the body medial portion deployed condition (79).

Again referring primarily to FIG. 12A and FIG. 12B, the collapsible body medial portion (78) can further include at least one collapsible body medial portion recess (81) which can facilitate collapsing of the collapsible body medial portion (78) from the body medial portion deployed condition (79) toward the body medial portion collapsed condition (80). As to particular embodiments, the collapsible body medial portion recess (81) can be configured as a circumferential collapsible body medial portion recess (82), which can facilitate longitudinal collapsing of the collapsible body medial portion (78).

Again referring primarily to FIG. 12A and FIG. 12B, as to particular embodiments, the collapsible body medial portion (78) in the body medial portion collapsed condition (80) can be disposed within the body closed end portion interior space (77) bounded by the body closed end portion wall (54) to reduce the flexible tubular body volume of the flexible tubular body (2).

As to particular embodiments, the collapsible body medial portion (78) in the body medial portion collapsed condition (80) can be disposed within the body closed end portion interior space (77) bounded by the body closed end portion wall (54) by forcibly urging the collapsible body medial portion (78) in the body medial portion collapsed condition (80) into the body closed end portion interior space (77) bounded by the body closed end portion wall (54).

As to particular embodiments, suction (83) can be applied to facilitate the forcible urging of the collapsible body medial portion (78) in the body medial portion collapsed condition (80) into the body closed end portion interior space (77) bounded by the body closed end portion wall (54). As an illustrative example, longitudinal suction (84) can be applied proximate a body closed end portion end (85) of the body closed end portion (4) to facilitate the forcible urging of the collapsible body medial portion (78) in the body medial portion collapsed condition (80) into the body closed end portion interior space (77) bounded by the body closed end portion wall (54). As an additional illustrative example, lateral suction (86) can be applied proximate one or more body closed end portion sides (87) of the body closed end portion (4) to facilitate the forcible urging of the collapsible body medial portion (78) in the body medial portion collapsed condition (80) into the body closed end portion interior space (77) bounded by the body closed end portion wall (54).

As to particular embodiments, the body medial portion collapsed condition (80) can facilitate actuation of the collapsible body medial portion (78) toward the body medial portion deployed condition (79) when the body closed end portion (4) is inserted into the vaginal canal (9) toward a cervix (1) of a female user (10).

Now referring primarily to FIG. 13A through FIG. 18, a method of producing a protective sheath (1) can include providing a flexible tubular body (2) having a body medial portion (3) disposed between a body closed end portion (4) and a body open end portion (5) and extending an annular flange (6) radially outward from the body open end portion (5), whereby the annular flange (6) terminates in an annular flange edge (7) having an elliptical annular flange edge perimeter (8).

Now referring primarily to FIG. 13A through FIG. 17, as to particular embodiments, the method can further include producing the protective sheath (1) as a one-piece protective sheath construct (88) by forming a first coating (89) of a first material (90) on a former (91), the first coating (89) defining the flexible tubular body (2) having the body medial portion (3) disposed between the body closed end portion (4) and the body open end portion (5) and the annular flange (6) extending radially outward from the body open end portion (5), the annular flange (6) terminating in the annular flange edge (7) having the elliptical annular flange edge perimeter (8); and curing the first coating (89) on the former (91).

Again referring primarily to FIG. 13A through FIG. 17, as to particular embodiments, the method can further include forming a second coating (92) of a second material (93) on the former (91), the second coating (92) overlaying a portion of the first coating (89) defining the body closed end portion (4); and curing the second coating (92) on the former (91).

Again referring primarily to FIG. 13A through FIG. 17, as to particular embodiments, the method can further include forming a third coating (94) of a third material (95) on the former (91), the third coating (94) overlaying a portion of the first coating (89) defining the annular flange (6); and curing the third coating (94) on the former (91).

Again referring primarily to FIG. 13A through FIG. 17, as to particular embodiments, the method can further include forming a fourth coating (96) of a fourth material (97) on the former (91), the fourth coating (96) overlaying the second coating (92) defining the body closed end portion (4), the first coating (89) defining the body medial portion (3), and the third coating (94) defining the annular flange (6); and curing the fourth coating (96) on the former (91).

Now referring primarily to FIG. 13A through FIG. 14B and FIG. 16, as to particular embodiments, forming the first, second, third, or fourth coating (89)(92)(94)(96) of the corresponding first, second, third, or fourth material (90)(93)(95)(97) can further include dipping the former (91) into the corresponding first, second, third, or fourth material (90)(93)(95)(97). As to particular embodiments, the method can further include disposing a former longitudinal axis (98) of the former (91) in a generally vertical position prior to dipping the former (91) into the corresponding first, second, third, or fourth material (90)(93)(95)(97).

Now referring primarily to FIG. 15 and FIG. 16, as to particular embodiments, forming the first, second, third, or fourth coating (89)(92)(94)(96) of the corresponding first, second, third, or fourth material (90)(93)(95)(97) can further include depositing the corresponding first, second, third, or fourth material (90)(93)(95)(97) onto the former (91). As to particular embodiments, the method can further include disposing a former longitudinal axis (98) of the former (91) in a generally horizontal position relative to a material dispenser (99) prior to depositing the corresponding first, second, third, or fourth material (90)(93)(95)(97) onto the former (91), and rotating the former (91) about the former longitudinal axis (98) while depositing the corresponding first, second, third, or fourth material (90)(93)(95)(97) onto the former (91).

Now referring primarily to FIG. 18, as to particular embodiments, the method of producing the protective sheath (1) can include producing the protective sheath (1) from a plurality of discrete pieces (100). As to particular embodiments, the method can include providing the body medial portion (3) as a discrete body medial portion (101) having opposing discrete body medial portion first and second open ends (102)(103); providing the annular flange (6) as a discrete annular flange (104); coupling the discrete annular flange (104) to the discrete body medial portion (101) proximate the discrete body medial portion first open end (102); providing the body closed end portion (4) as a discrete body closed end portion (105); and coupling the discrete body closed end portion (105) to the discrete body medial portion (101) proximate the discrete body medial portion second open end (103).

Again referring primarily to FIG. 18, as to particular embodiments, coupling the discrete annular flange (104) to the discrete body medial portion (101) can include adhering the discrete annular flange (104) to the discrete body medial portion (101) with a first adherent layer (106); and coupling the discrete body closed end portion (105) to the discrete body medial portion (101) can include adhering the discrete body closed end portion (105) to the discrete body medial portion (101) with a second adherent layer (107).

Again referring primarily to FIG. 18, coupling the discrete annular flange (104) to the discrete body medial portion (101) can include joining the discrete annular flange (104) to the discrete body medial portion (101) with a first joining process (108), for example using temperature, pressure, or the like, or combinations thereof; and coupling the discrete body closed end portion (105) to the discrete body medial portion (101) can include joining the discrete body closed end portion (105) to the discrete body medial portion (101) with a second joining process (109), for example using temperature, pressure, or the like, or combinations thereof.

Now referring primarily to FIG. 6A through FIG. 8B, as to particular embodiments, the method of producing the protective sheath (1) can further include forming a bead element (31) extending around the elliptical annular flange edge perimeter (8).

Figure 6B:
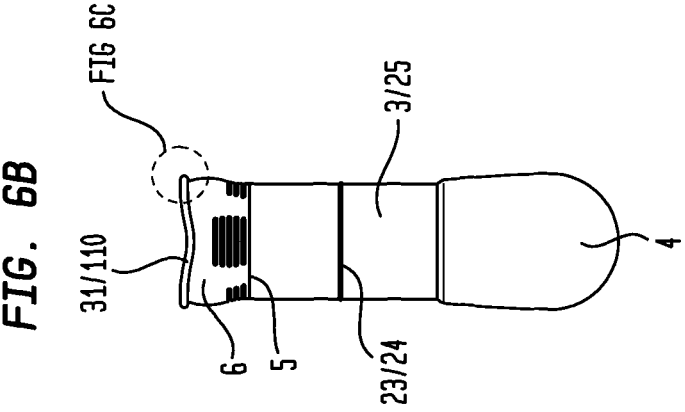
FIG. 6B is a view of a particular embodiment of a protective sheath including a bead element having a generally circular bead element cross section.
Figure 6A:
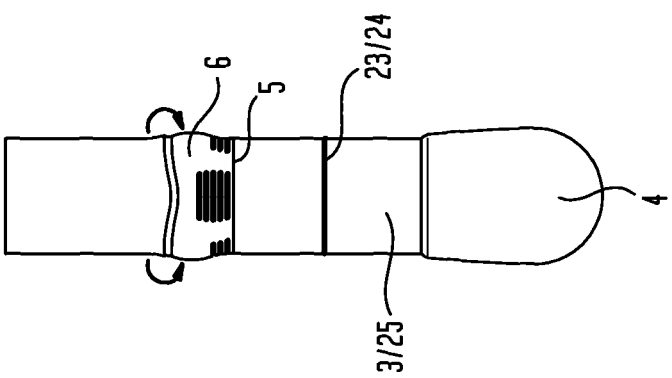
FIG. 6A is an illustration of a particular method of forming a bead element on a protective sheath, whereby the bead element has generally circular cross section.

Now referring primarily to FIG. 6A through FIG. 6C, the bead element (31) can have a generally circular bead element cross-section (33), whereby the method of forming the bead element (31) having the generally circular bead element cross-section (33) can include rolling a portion of the annular flange (6) upon itself to provide a rolled bead element (110).

As to particular embodiments, the rolled bead element (110) can include an adherent element which precludes the rolled bead element (110) from unrolling.

As to other particular embodiments, the rolled bead element (110) can be precluded from unrolling by cross-linking bonds generated in the material which forms the rolled bead element (110), for example by curing the rolled bead element (110) at a temperature and for a period of time which is sufficient to generate cross-linking bonds in the material which forms the rolled bead element (110).

Now referring primarily to FIG. 7A through FIG. 8B, the bead element (31) can have a generally semi-circular bead element cross section (34), whereby a generally planar bead element portion (35) of the bead element (31) having the generally semi-circular bead element cross section (34) can dispose proximate an annular flange opening (36) bounded by the annular flange edge (7).

Now referring primarily to FIG. 7A through FIG. 7C, the method of forming the bead element (31) having the generally semi-circular bead element cross-section (34) can include disposing an elastic annular member (111) about the annular flange (6) and overlaying an annular flange overlaying portion (112) of the annular flange (6) over an elastic annular member outer surface (113) of the elastic annular member (111).

As to particular embodiments, disposing the elastic annular member (111) about the annular flange (6) and overlaying the annular flange overlaying portion (112) over the elastic annular member outer surface (113) can be performed while the protective sheath (1) disposes on the former (91) which forms the protective sheath (1) during the manufacturing process.

Now referring primarily to FIG. 8A and FIG. 8B, the method of forming the bead element (31) having the generally semi-circular bead element cross-section (34) can include circumferentially depositing the bead element (31) about an annular flange outer surface (50) of the annular flange (6) proximate the annular flange edge (7).

Now referring primarily to FIG. 8A, as to particular embodiments, the bead element (31) can be circumferentially deposited about the annular flange outer surface (50) of the annular flange (6) proximate the annular flange edge (7) during the manufacturing process, for example while a former longitudinal axis (98) of the former (91) disposes in a generally horizontal position relative to a bead element dispenser (114), the former (91) rotating about the former longitudinal axis (98) during the circumferential deposition of the bead element (31) to deposit the bead element (31) about the annular flange outer surface (50) proximate the annular flange edge (7).

As to particular embodiments, the method of producing the protective sheath (1) can further include coupling a body medial portion retention element (23) to the body medial portion (3). As to particular embodiments, the method can further include configuring the body medial portion retention element (23) as a body medial portion circumferential protrusion (24) which outwardly extends from a body medial portion outer surface (25) of the body medial portion (3).

As to particular embodiments, the body medial portion circumferential protrusion (24) can be formed by disposing an elastic annular member (111) about the body medial portion (3).

As to particular embodiments, the body medial portion circumferential protrusion (24) can be formed by circumferentially depositing the body medial portion circumferential protrusion (24) about the body medial portion (3), for example via a body medial portion circumferential protrusion dispenser.

Now referring primarily to FIG. 1A and FIG. 1B, a method of using the protective sheath (1) within a vaginal canal (9) of a female user (10) can include obtaining the protective sheath (1) including a flexible tubular body (2) having a body medial portion (3) disposed between a body closed end portion (4) and a body open end portion (5); and an annular flange (6) extending radially outward from the body open end portion (5), the annular flange (6) terminating in an annular flange edge (7) having an elliptical annular flange edge perimeter (8); inserting the body closed end portion (4) into the vaginal canal (9) toward a cervix (11) of the female user (10); and engaging a portion of a vulva (12) of the female user (10) with the annular flange edge (7) to preclude the annular flange edge (7) from ingress into the vaginal canal (9). As to particular embodiments, the method can further include stimulating the vulva (12) of the female user (10) with the annular flange edge (7).

Although the above description describes the elements of the protective sheath (1) in relation to a protective sheath (1) for use within a vaginal canal (9) of a female user (10), the invention need not be so limited, as the elements of the protective sheath (1) and methods of producing elements of the protective sheath (1) can further be applied to other embodiments of protective sheaths, such as male condoms, finger cots, probe covers, polymeric gloves (for example, disposable gloves), or the like, or combinations thereof.

An illustrative example of an element of the protective sheath (1) which can be applied to other embodiments of protective sheaths can include a bead element (31) extending around an edge perimeter (115) of an edge (116) bounding an opening (117), the bead element (31) including a generally semi-circular bead element cross section (34), whereby a generally planar bead element portion (35) of the bead element (31) having the generally semi-circular bead element cross section (34) disposes proximate the opening (117) bounded by the edge (116).

Another illustrative example of an element of the protective sheath (1) which can be applied to other embodiments of protective sheaths can include a bead element (31) extending around an edge perimeter (115) of an edge bounding (116) an opening (117), the bead element (31) including a texture element (37) coupled to the bead element (31).

Another illustrative example of an element of the protective sheath (1) which can be applied to other embodiments of protective sheaths can include a bead element (31) extending around an edge perimeter (115) of an edge (116) bounding an opening (117), the bead element (31) comprising a non-planar bead element perimeter (40).

An illustrative example of a method of producing an element of the protective sheath (1) which can be applied to other embodiments of protective sheaths can include a method of forming a bead element (31) which extends around an edge perimeter (115) of an edge (116) bounding an opening (117), the method including disposing an elastic annular member (111) about the edge (116) and overlaying an edge overlaying portion (118) of the edge (116) over an elastic annular member outer surface (113) of the elastic annular member (111) to provide the bead element (31) having a generally semi-circular bead element cross section (34), whereby a generally planar bead element portion (35) of the bead element (31) having the generally semi-circular bead element cross section (34) disposes proximate the opening (117) bounded by the edge (116).

Another illustrative example of a method of producing an element of the protective sheath (1) which can be applied to other embodiments of protective sheaths can include a method of forming a bead element (31) which extends around an edge perimeter (115) of an edge (116) bounding an opening (117), the method including circumferentially depositing the bead element (31) about the edge (116) to provide the bead element (31) having a generally semi-circular bead element cross section (34), whereby a generally planar bead element portion (35) of the bead element (31) having the generally semi-circular bead element cross section (34) disposes proximate the opening (117) bounded by the edge (116).

Another illustrative example of a method of producing an element of the protective sheath (1) which can be applied to other embodiments of protective sheaths can include a method of forming a retention element (119) configured as a circumferential protrusion (120) which outwardly extends from a body (121), the method including disposing an elastic annular member (111) about the body (121).

Another illustrative example of a method of producing an element of the protective sheath (1) which can be applied to other embodiments of protective sheaths can include a method of forming a retention element (119) configured as a circumferential protrusion (120) which outwardly extends from a body (121), the method including circumferentially depositing the circumferential protrusion (120) about the body (121).

Now referring primarily to FIG. 19, an additional embodiment of a protective sheath (1) includes a flexible tubular body (122) including a body medial portion (123) having opposing body medial portion first and second open ends (124)(125), the body medial portion second open end (125) having a body medial portion second open end diameter (126); a discrete body end portion (127) having opposing discrete body end portion open and closed ends (128)(129), the discrete body end portion open end (128) having a discrete body end portion open end diameter (130); whereby the discrete body end portion open end diameter (130) is greater than the body medial portion second open end diameter (126); and whereby the discrete body end portion open end (128) couples to the body medial portion second open end (125).

Again referring primarily to FIG. 19, as to particular embodiments, the discrete body end portion (127) can be configured as a bulbous discrete body end portion (131).

As to particular embodiments, the discrete body end portion open end (128) can dispose a distance of at least about 60 millimeters from the body medial portion first open end (124) to facilitate retention of the discrete body end portion (127) within the vaginal canal (9) proximate the cervix (11) of a female user (10), particularly during coitus. As an illustrative example, a discrete body end portion open end (128) which disposes a distance of about 90 millimeters from the body medial portion first open end (124) can position the discrete body end portion (127) a distance of about 90 millimeters within the vaginal canal (9) toward the cervix (11) of the female user (10) to facilitate retention of the discrete body end portion (127) within the vaginal canal (9).

As to particular embodiments, the discrete body end portion open end (128) can dispose a distance of less than about 80 millimeters from the body medial portion second open end (125). As to particular embodiments, the distance can be selected from the group including or consisting of: less than about 80 millimeters; less than about 75 millimeters; less than about 70 millimeters; less than about 65 millimeters; less than about 60 millimeters; less than about 55 millimeters; less than about 50 millimeters; less than about 45 millimeters; less than about 40 millimeters; less than about 35 millimeters; less than about 30 millimeters; less than about 25 millimeters; less than about 20 millimeters; less than about 15 millimeters; less than about 10 millimeters; and less than about 5 millimeters; whereby a lesser distance provides a lesser angle (132) between the body medial portion second open end diameter (126) and the discrete body end portion open end diameter (130) in relation to a greater distance, which provides a greater angle between the body medial portion second open end diameter (126) and the discrete body end portion open end diameter (130) (as shown in the example of FIG. 19).

As to particular embodiments, the discrete body end portion (127) can further include a discrete body end portion wall (133) having a discrete body end portion wall durometer (134) which is greater than a body medial portion wall durometer (135) of a body medial portion wall (136) of the body medial portion (123).

As to particular embodiments, the discrete body end portion (127) can further include a discrete body end portion wall (133) having a discrete body end portion wall thickness (137) which is greater than a body medial portion wall thickness (138) of a body medial portion wall (136) of the body medial portion (123).

As to particular embodiments, the protective sheath (1) can further include an annular flange (6) extending radially outward from the body medial portion first open end (124), the annular flange (6) terminating in an annular flange edge (7) having an elliptical annular flange edge perimeter (8), as described above.

As to particular embodiments, the annular flange edge (7) having the elliptical annular flange edge perimeter (8) can be configured to overlay a portion of a vulva (12) of a female user (10) when the protective sheath (1) is used by the female user (10), as described above.

A method of producing an additional embodiment of the protective sheath (1) includes providing a flexible tubular body (122) including a body medial portion (123) having opposing body medial portion first and second open ends (124)(125), the body medial portion second open end (125) having a body medial portion second open end diameter (126); providing a discrete body end portion (127) having opposing discrete body end portion open and closed ends (128)(129), the discrete body end portion open end (128) having a discrete body end portion open end diameter (130); whereby the discrete body end portion open end diameter (130) is greater than the body medial portion second open end diameter (126); and coupling the discrete body end portion open end (128) to the body medial portion second open end (125).

As to particular embodiments, the method of producing the additional embodiment of the protective sheath (1) can further include producing the protective sheath (1) as a one-piece protective sheath construct (88), as described above, which can include one or more elements as described above.

As to other particular embodiments, the method of producing the additional embodiment of the protective sheath (1) can further include producing the protective sheath (1) from a plurality of discrete pieces, as described above, which can include one or more elements as described above.

As can be easily understood from the foregoing, the basic concepts of the present invention may be embodied in a variety of ways. The invention involves numerous and varied embodiments of a protective sheath and methods for making and using such protective sheaths including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "protector" should be understood to encompass disclosure of the act of "protecting"—whether explicitly discussed or not—and, conversely, were there effectively disclosure of the act of "protecting", such a disclosure should be understood to encompass disclosure of a "protector" and even a "means for protecting". Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the protective sheaths herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A protective sheath for a female user, comprising,
a flexible tubular body having a body medial portion disposed between a body closed end portion and a body open end;
an annular flange extending radially outward from said body open end, said annular flange having a funnel shape, and said annular flange terminating in an annular flange edge having an elliptical annular flange edge perimeter; wherein said annular flange edge having said elliptical annular flange edge perimeter is configured to overlay a portion of a vulva of said female user; an arcuate element extending radially outward from said elliptical annular flange edge perimeter, said arcuate element and said elliptical annular flange edge perimeter forming a continuous perimeter of the funnel-shaped annular flange; an annular flange portion defined by said arcuate element and said annular flange; and
a first protrusion outwardly extending from said annular flange portion toward said body closed end portion, said first protrusion configured to engage a clitoris of said female user.

2. The protective sheath of claim 1, wherein said first protrusion has a configuration selected from the group consisting of: one or more generally circular protrusions, one or more generally elliptical protrusions, one or more generally polygonal protrusions, one or more generally linear protrusions, one or more arcuate protrusions, or combinations thereof.

3. The protective sheath of claim 1, further comprising a second protrusion outwardly extending from said annular flange, said second protrusion configured to engage a right labial portion of said vulva of said female user.

4. The protective sheath of claim 3, further comprising a third protrusion outwardly extending from said annular flange, said third protrusion is configured to engage a left labial portion of said vulva of said female user.

5. The protective sheath of claim 4, further comprising a fourth protrusion outwardly extending from said annular flange, said fourth protrusion configured to engage a portion of a perineum of said female user.

6. The protective sheath of claim 1, wherein said elliptical annular flange edge perimeter is greater than a body medial portion perimeter of said body medial portion.

7. The protective sheath of claim 1, wherein said body closed end portion comprises a body closed end portion wall having a body closed end portion wall durometer which is greater than a body medial portion wall durometer of a body medial portion wall of said body medial portion.

8. The protective sheath of claim 1, wherein said body closed end portion further comprises a body closed end portion perimeter which is greater than a body medial portion perimeter of said body medial portion.

9. The protective sheath of claim 1, wherein said body closed end portion further comprises a body closed end portion perimeter which is lesser than a body medial portion perimeter of said body medial portion.

10. The protective sheath of claim 1, wherein said body closed end portion further comprises at least one body closed end portion retention element.

11. The protective sheath of claim 1, wherein said body medial portion is configured as a collapsible body medial portion, said collapsible body medial portion collapsible from a body medial portion deployed condition toward a body medial portion collapsed condition in which said collapsible body medial portion occupies a lesser volume of space in relation to said body medial portion deployed condition.

12. The protective sheath of claim 1, wherein said flexible tubular body is formed from one or more materials selected from the group consisting of: polymeric materials, natural rubber latex, acrylonitrile butadiene rubber, polyisoprene latex, polyvinyl chloride, polychloroprene rubber, and polyurethane.

13. The protective sheath of claim 1, wherein said annular flange edge terminates in a bead element.

14. The protective sheath of claim 1, wherein said annular flange outwardly flares from said body open end to dispose said annular flange edge axially away from said body medial portion.

15. The protective sheath of claim 1, wherein said annular flange portion has the same wall thickness as said annular flange.

16. The protective sheath of claim 1, wherein said annular flange is nonplanar between said body open end and said annular flange edge.

17. A method of using a protective sheath within a vaginal canal of a female user, comprising:
   obtaining said protective sheath comprising:
      a flexible tubular body having a body medial portion disposed between a body closed end portion and a body open end;
      an annular flange extending radially outward from said body open end, said annular flange having a funnel shape, and said annular flange terminating in an annular flange edge having an elliptical annular flange edge perimeter; and an arcuate element extending radially outward from said elliptical annular flange edge perimeter, said arcuate element and said elliptical annular flange edge perimeter forming a continuous perimeter of the funnel-shaped annular flange; and an annular flange portion defined by said arcuate element and said annular flange;
   inserting said body closed end portion into said vaginal canal toward a cervix of said female user;
   engaging a portion of a vulva of said female user with said annular flange edge to preclude said annular flange edge from ingress into said vaginal canal; and
   engaging a clitoris of said female user with said annular flange portion to facilitate stimulation of said clitoris.

18. A protective sheath for a female user, comprising,
   a flexible tubular body having a body medial portion disposed between a body closed end portion and a body open end;
   an annular flange extending radially outward from said body open end, said annular flange having a funnel shape, and said annular flange terminating in an annular flange edge having an elliptical annular flange edge; an arcuate element extending radially outward from said elliptical annular flange edge, said arcuate element and said elliptical annular flange edge forming a continuous edge of the funnel-shaped annular flange; an annular flange portion defined by said arcuate element and said annular flange;
   and
   a first protrusion outwardly extending from said annular flange portion toward said body closed end portion.

19. The protective sheath of claim 18, wherein said body closed end portion further comprises a body closed end portion perimeter which is greater than a body medial portion perimeter of said body medial portion.

20. The protective sheath of claim 18, wherein said body closed end portion further comprises a body closed end portion perimeter which is lesser than a body medial portion perimeter of said body medial portion.

* * * * *